United States Patent
Fabbri et al.

(10) Patent No.: US 11,960,795 B2
(45) Date of Patent: Apr. 16, 2024

(54) NEURAL NETWORK-BASED GENERATION AND PLACEMENT OF TOOTH RESTORATION DENTAL APPLIANCES

(71) Applicant: 3M INNOVATIVE PROPERTIES COMPANY, St. Paul, MN (US)

(72) Inventors: Cameron M. Fabbri, St. Paul, MN (US); Jonathan D. Gandrud, Woodbury, MN (US); Joseph C. Dingeldein, Hudson, WI (US); James D. Hansen, White Bear Lake, MN (US); Benjamin D. Zimmer, Hudson, WI (US); Jianbing Huang, Shoreview, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 17/917,211

(22) PCT Filed: May 14, 2021

(86) PCT No.: PCT/IB2021/054151
§ 371 (c)(1),
(2) Date: Oct. 5, 2022

(87) PCT Pub. No.: WO2021/240290
PCT Pub. Date: Dec. 2, 2021

(65) Prior Publication Data
US 2023/0153476 A1     May 18, 2023

Related U.S. Application Data

(60) Provisional application No. 63/030,144, filed on May 26, 2020.

(51) Int. Cl.
*G06F 30/10* (2020.01)
*A61C 13/00* (2006.01)
(Continued)

(52) U.S. Cl.
CPC .......... *G06F 30/10* (2020.01); *A61C 13/0004* (2013.01); *A61C 13/34* (2013.01); *G06T 17/20* (2013.01)

(58) Field of Classification Search
CPC ..... G06F 30/10; A61C 13/0004; A61C 13/34; G06T 17/20; G06T 19/20
See application file for complete search history.

(56) References Cited

U.S. PATENT DOCUMENTS 8,896,592 B2 * 11/2014 Boltunov ................ G06T 19/20
433/199.1
10,517,482 B2 * 12/2019 Sato ...................... A61B 5/0066
(Continued)

FOREIGN PATENT DOCUMENTS

| EP | 3503038 A1 | 6/2019 |
| EP | 3620130 A1 | 3/2020 |
| WO | 2020240351 A1 | 12/2020 |

OTHER PUBLICATIONS

International Search Report for PCT International Application No. PCT/IB2021/054151 dated Aug. 11, 2021, 5 pages.

*Primary Examiner* — Nicholas D Lucchesi
(74) *Attorney, Agent, or Firm* — Sriram Srinivasan

(57) ABSTRACT

Techniques are described for automating the design of dental restoration appliances using neural networks. An example computing device receives transform information associated with a current dental anatomy of a dental restoration patient, provides the transform information associated with the current dental anatomy of the dental restoration patient as input to a neural network trained with transform information indicating placement of a dental appliance component with respect to one or more teeth of corresponding dental anatomies, the dental appliance being used for dental restoration treatment for the one or more teeth, and executes the neural network using the input to produce placement information (Continued)

for the dental appliance component with respect to the current dental anatomy of the dental restoration patient.

15 Claims, 23 Drawing Sheets

(51) Int. Cl.
*A61C 13/34* (2006.01)
*G06T 17/20* (2006.01)

(56) References Cited

U.S. PATENT DOCUMENTS

| | | | |
|---|---|---|---|
| 10,561,476 B2 * | 2/2020 | Matov | G06F 30/20 |
| 11,191,618 B1 * | 12/2021 | Raslambekov | G06T 17/10 |
| 11,426,260 B1 * | 8/2022 | Raslambekov | A61C 9/0046 |
| 11,621,069 B2 * | 4/2023 | Raslambekov | B29C 64/386 |
| | | | 700/118 |
| 11,653,999 B2 * | 5/2023 | Raslambekov | A61C 13/0018 |
| | | | 700/98 |
| 2018/0028294 A1 | 2/2018 | Azernikov et al. | |
| 2018/0263732 A1 | 9/2018 | Pokotilov et al. | |
| 2019/0180443 A1 | 6/2019 | Xue et al. | |
| 2019/0282344 A1 | 9/2019 | Azernikov et al. | |
| 2019/0350680 A1 | 11/2019 | Chekh et al. | |
| 2020/0085546 A1 | 3/2020 | Li et al. | |
| 2020/0320685 A1 * | 10/2020 | Anssari Moin | G06V 10/454 |

* cited by examiner

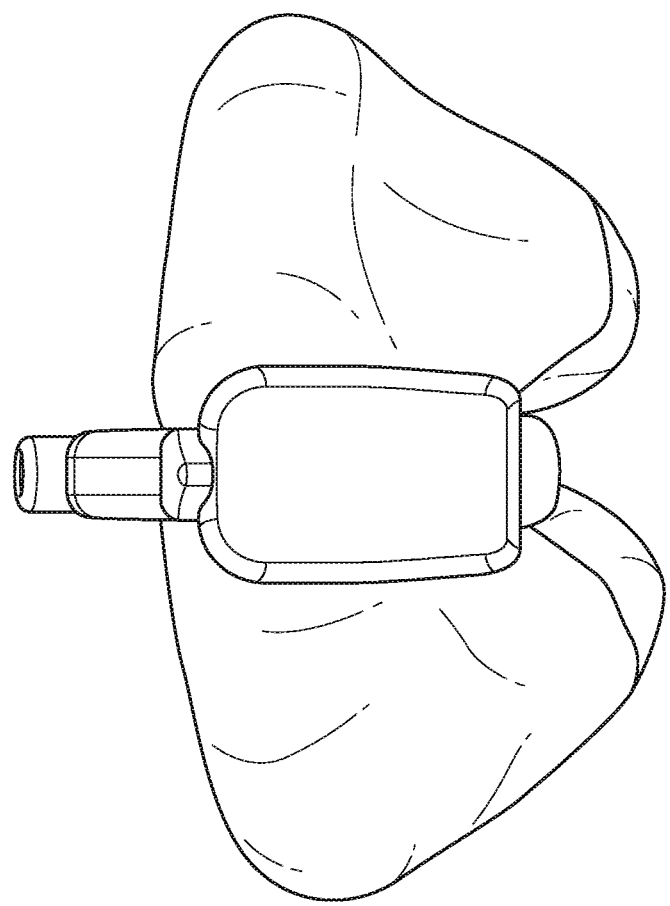
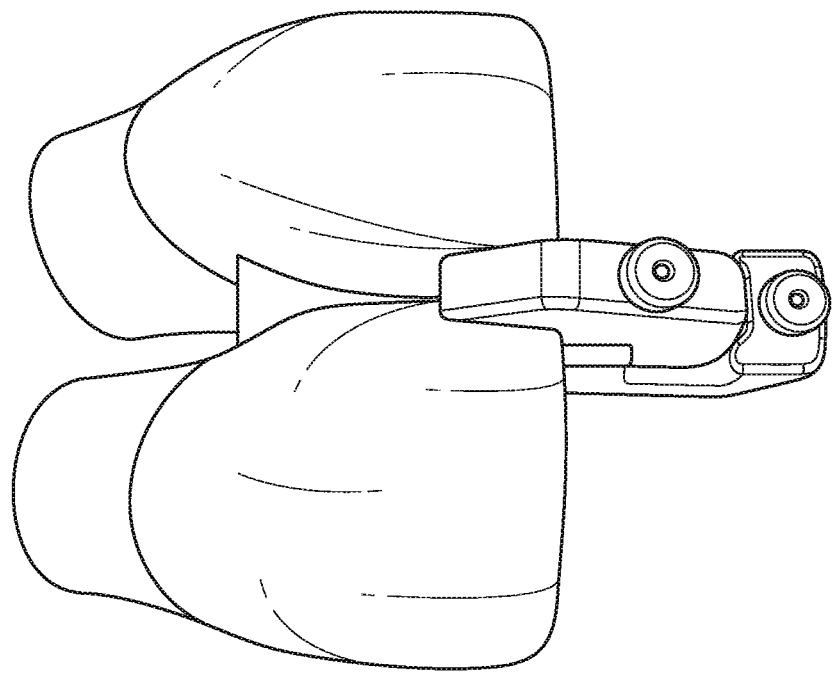
FIG. 6

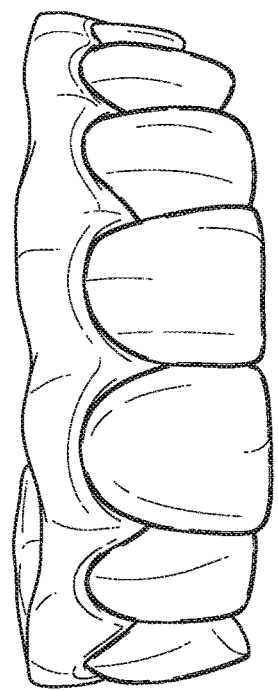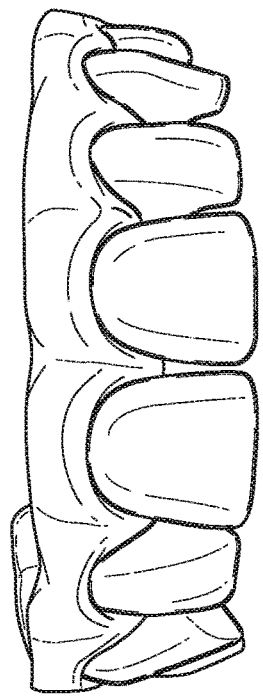
FIG. 11A

NEURAL NETWORK-BASED GENERATION AND PLACEMENT OF TOOTH RESTORATION DENTAL APPLIANCES

CROSS-REFERENCE TO RELATED APPLICATIONS

This application is a national stage filing under 35 U.S.C. 371 of PCT/IB202/054151, filed 14 May 2021, which claims the benefit of Provisional Application No. 63/030,144, filed 26 May 2020, the entire disclosure of each of which is incorporated herein by reference.

TECHNICAL FIELD

The present disclosure relates to dental restoration appliances used for reshaping teeth.

BACKGROUND

Dental practitioners often utilize dental appliances to re-shape or restore a patient's dental anatomy. The dental appliance is typically constructed from a model of the patient's dental anatomy, augmented to a desired dental anatomy. The model may be a physical model or a digital model. Designing the dental appliance is often a manual, time-consuming, and inexact process. For example, a practitioner typically designs a model of the dental appliance by trial and error. For instance, the practitioner may add, remove, reposition, rearrange, and/or resize features until the practitioner is satisfied with the model of the dental appliance.

SUMMARY

The disclosure relates to techniques for automating a design of a dental restoration appliance for restoring the dental anatomy of a given patient and/or a proposed placement of a dental restoration appliance for the dental restoration treatment of the patient. Computing systems configured according to aspects of this disclosure implement neural network-based systems trained with any of a variety of datasets to generate design aspects (or "geometry") of a dental restoration appliance for a particular patient and/or the placement characteristics (or "transform") of the dental restoration appliance for a particular patient. To generate a custom geometry of a patient-specific dental restoration appliance and/or transform information thereof, the computing systems of this disclosure implement neural networks trained with dental anatomy and/or dental appliance information available from digital libraries of predefined appliance geometries and/or pre-made appliance "ground truths" (e.g. appliance geometries that were created manually by a skilled practitioner or created automatically via the rules-based system described in WO 2020/240351, filed May 20, 2020, the entire content of which is incorporated herein by reference).

The geometry of a dental appliance is represented by a digital three-dimensional (3D) mesh incorporating the features of the generated geometry. In various examples, the neural network-based techniques of this disclosure may generate a new geometry based on the patient's dental anatomy and on the dataset(s) of "ground truth" appliance geometries with which the neural network is trained. In some examples, the neural network-based techniques of this disclosure may generate placement data for a geometry which is selected from a digital library of dental appliance geometries, and then based on the patient's dental anatomy and based on the dataset(s) of transformation matrices with which the neural network is trained, place that library geometry relative to or more of the patient's teeth.

In some examples, the neural network-based techniques of this disclosure may generate placement data for a dental appliance which is selected from a digital library of dental appliance geometries. Examples of placement data may relate to one or more of the position, the orientation, the scale, or shear mapping of the dental appliance as it is to be placed during dental restoration treatment of the patient. The computing systems of this disclosure may implement a simple neural network (e.g., with a relatively small number of hidden layers or no hidden layers), a graph convolutional neutral network (GCNN), a generative adversarial network (GAN), a conditional generative adversarial network (cGAN), an encoder-decoder based CNN, a U-Net CNN, a GAN with a PatchGAN discriminator, and/or another deep neutral network (DNN) to perform various techniques described herein.

In this way, the computing systems of this disclosure train and execute neural networks to automate the selection/generation of dental appliance component 3D meshes as well as the placement of dental appliance library component 3D meshes, all of which are later combined and assembled into a completed dental appliance. The computing systems of this disclosure may train the neural networks using a variety of data, such as dental anatomy landmarks, patient-to-mesh mappings, two-dimensional (2D) dental anatomy images, etc. to define a dental restoration appliance component and its placement. The geometry and placement information generated by the neural networks trained with the dataset(s) selected according to the techniques of this disclosure automatically generate a mesh (a 3D digital custom model) which can be used to manufacture the patient-specific dental restoration appliance, such as by 3D printing the restoration appliance from the mesh.

In one example, a computing device includes an input interface and a neural network engine. The input interface is configured to receive transform information associated with a current dental anatomy of a dental restoration patient. The neural network engine configured to provide the transform information associated with the current dental anatomy of the dental restoration patient as input to a neural network trained with transform information indicating placement of a dental appliance component with respect to one or more teeth of corresponding dental anatomies, the dental appliance being used for dental restoration treatment for the one or more teeth. The neural network engine is further configured to execute the neural network using the input to produce placement information for the dental appliance component with respect to the current dental anatomy of the dental restoration patient.

In another example, a method includes receiving transform information associated with a current dental anatomy of a dental restoration patient. The method further includes providing the transform information associated with the current dental anatomy of the dental restoration patient as input to a neural network trained with transform information indicating placement of a dental appliance component with respect to one or more teeth of corresponding dental anatomies, the dental appliance being used for dental restoration treatment for the one or more teeth. The method further includes executing the neural network using the input to produce placement information for the dental appliance component with respect to the current dental anatomy of the dental restoration patient.

In another example, an apparatus includes means for receiving transform information associated with a current dental anatomy of a dental restoration patient, means for providing the transform information associated with the current dental anatomy of the dental restoration patient as input to a neural network trained with transform information indicating placement of a dental appliance component with respect to one or more teeth of corresponding dental anatomies, the dental appliance being used for dental restoration treatment for the one or more teeth, and means for executing the neural network using the input to produce placement information for the dental appliance component with respect to the current dental anatomy of the dental restoration patient.

In another example, a non-transitory computer-readable storage medium is encoded with instructions. The instructions, when executed, cause one or more processors of a computing system to receive transform information associated with a current dental anatomy of a dental restoration patient, to provide the transform information associated with the current dental anatomy of the dental restoration patient as input to a neural network trained with transform information indicating placement of a dental appliance component with respect to one or more teeth of corresponding dental anatomies, the dental appliance being used for dental restoration treatment for the one or more teeth, and to execute the neural network using the input to produce placement information for the dental appliance component with respect to the current dental anatomy of the dental restoration patient.

In one example, a computing device includes an input interface and a neural network engine. The input interface is configured to receive one or more three-dimensional (3D) tooth meshes associated with a current dental anatomy of a dental restoration patient and a 3D component mesh representing a generated geometry for a dental appliance component. The neural network engine configured to provide the one or more 3D tooth meshes and the 3D component mesh received by the input interface as inputs to a neural network trained with training data comprising ground truth dental appliance component geometries and 3D tooth meshes of corresponding dental restoration cases. The neural network engine is further configured to execute the neural network using the provided inputs to produce an updated model of the dental appliance component with respect to the current dental anatomy of the dental restoration patient.

In another example, a method includes receiving, at an input interface, one or more three-dimensional (3D) tooth meshes associated with a current dental anatomy of a dental restoration patient and a 3D component mesh representing a generated geometry for a dental appliance component. The method further includes providing, by a neural network engine communicatively coupled to the input interface, the one or more 3D tooth meshes and the 3D component mesh received by the input interface as inputs to a neural network trained with training data comprising ground truth dental appliance component geometries and 3D tooth meshes of corresponding dental restoration cases. The method further includes executing, by the neural network engine, the neural network using the provided inputs to produce an updated model of the dental appliance component with respect to the current dental anatomy of the dental restoration patient.

In another example, an apparatus includes means for receiving one or more three-dimensional (3D) tooth meshes associated with a current dental anatomy of a dental restoration patient and a 3D component mesh representing a generated geometry for a dental appliance component, means for providing the one or more 3D tooth meshes and the 3D component mesh received by the input interface as inputs to a neural network trained with training data comprising ground truth dental appliance component geometries and 3D tooth meshes of corresponding dental restoration cases, and means for executing the neural network using the provided inputs to produce an updated model of the dental appliance component with respect to the current dental anatomy of the dental restoration patient.

In another example, a non-transitory computer-readable storage medium is encoded with instructions. The instructions, when executed, cause one or more processors of a computing system to receive one or more three-dimensional (3D) tooth meshes associated with a current dental anatomy of a dental restoration patient and a 3D component mesh representing a generated geometry for a dental appliance component, to provide the one or more 3D tooth meshes and the 3D component mesh received by the input interface as inputs to a neural network trained with training data comprising ground truth dental appliance component geometries and 3D tooth meshes of corresponding dental restoration cases, and to execute the neural network using the provided inputs to produce an updated model of the dental appliance component with respect to the current dental anatomy of the dental restoration patient.

In one example, a computing device includes an input interface and a neural network engine. The input interface is configured to receive a two-dimensional (2D) image of a current dental anatomy of a dental restoration patient. The neural network engine configured to provide the 2D image of the current dental anatomy of the dental restoration patient as an input to a neural network trained with training data comprising 2D images of pre-restoration dental anatomies and corresponding 2D images of post-restoration dental anatomies of previously performed dental restoration cases. The neural network engine is further configured to execute the neural network using the input to produce a 2D image of a proposed dental anatomy of the dental restoration patient, the proposed dental anatomy being associated with a post-restoration outcome of a dental restoration plan for the dental restoration patient.

In another example, a method includes receiving a two-dimensional (2D) image of a current dental anatomy of a dental restoration patient. The method further includes providing the 2D image of the current dental anatomy of the dental restoration patient as an input to a neural network trained with training data comprising 2D images of pre-restoration dental anatomies and corresponding 2D images of post-restoration dental anatomies of previously performed dental restoration cases. The method further includes executing the neural network using the input to produce a 2D image of a proposed dental anatomy of the dental restoration patient, the proposed dental anatomy being associated with a post-restoration outcome of a dental restoration plan for the dental restoration patient.

In another example, an apparatus includes means for receiving a two-dimensional (2D) image of a current dental anatomy of a dental restoration patient, means for providing the 2D image of the current dental anatomy of the dental restoration patient as an input to a neural network trained with training data comprising 2D images of pre-restoration dental anatomies and corresponding 2D images of post-restoration dental anatomies of previously performed dental restoration cases, and means for executing the neural network using the input to produce a 2D image of a proposed dental anatomy of the dental restoration patient, the proposed dental anatomy being associated with a post-restoration outcome of a dental restoration plan for the dental restoration patient.

In another example, a non-transitory computer-readable storage medium is encoded with instructions. The instructions, when executed, cause one or more processors of a computing system to receive a two-dimensional (2D) image of a current dental anatomy of a dental restoration patient, to provide the 2D image of the current dental anatomy of the dental restoration patient as an input to a neural network trained with training data comprising 2D images of pre-restoration dental anatomies and corresponding 2D images of post-restoration dental anatomies of previously performed dental restoration cases, and to execute the neural network using the input to produce a 2D image of a proposed dental anatomy of the dental restoration patient, the proposed dental anatomy being associated with a post-restoration outcome of a dental restoration plan for the dental restoration patient.

In one example, a computing device includes an input interface and a neural network engine. The input interface is configured to receive one or more three-dimensional (3D) tooth meshes associated with a current dental anatomy of a dental restoration patient. The neural network engine configured to provide the one or more 3D tooth meshes received by the input interface as input to a neural network trained with training data comprising ground truth dental appliance component geometries and 3D tooth meshes of corresponding dental restoration cases. The neural network engine is further configured to execute the neural network using the provided input to produce a custom geometry for the dental appliance component with respect to the current dental anatomy of the dental restoration patient.

In another example, a method includes receiving one or more three-dimensional (3D) tooth meshes associated with a current dental anatomy of a dental restoration patient. The method further includes providing the one or more 3D tooth meshes associated with the current dental anatomy of the dental restoration patient as input to a neural network trained with training data comprising ground truth dental appliance component geometries and 3D tooth meshes of corresponding dental restoration cases. The method further includes executing the neural network using the provided input to produce a custom geometry for the dental appliance component with respect to the current dental anatomy of the dental restoration patient.

In another example, an apparatus includes means for receiving one or more three-dimensional (3D) tooth meshes associated with a current dental anatomy of a dental restoration patient, means for providing the one or more 3D tooth meshes associated with the current dental anatomy of the dental restoration patient as input to a neural network trained with training data comprising ground truth dental appliance component geometries and 3D tooth meshes of corresponding dental restoration cases, and means for executing the neural network using the provided input to produce a custom geometry for the dental appliance component with respect to the current dental anatomy of the dental restoration patient.

In another example, a non-transitory computer-readable storage medium is encoded with instructions. The instructions, when executed, cause one or more processors of a computing system to receive one or more three-dimensional (3D) tooth meshes associated with a current dental anatomy of a dental restoration patient, to provide the one or more 3D tooth meshes associated with the current dental anatomy of the dental restoration patient as input to a neural network trained with training data comprising ground truth dental appliance component geometries and 3D tooth meshes of corresponding dental restoration cases, and to execute the neural network using the provided input to produce a custom geometry for the dental appliance component with respect to the current dental anatomy of the dental restoration patient.

The techniques and practical applications described herein may provide certain advantages. For example, by automatically determining the geometry and placement of a 3D mesh to form a component of a dental appliance or a 3D mesh to form an overall model of a dental appliance for restorative treatment of a patient, the computing systems of this disclosure may improve data precision and conserve resources. For instance, by generating a more accurate 3D mesh component for the dental appliance, the computing systems of this disclosure may improve the functionality and efficacy of the dental appliance when used for restorative treatment.

In instances in which the computing systems utilize a reduced-layer neural network to predict placement information for the dental appliance, the computing systems may mitigate computational resource usage, by implementing a neural network with fewer hidden layers. In instances in which the computing systems utilize a GAN, GCNN, cGAN, an encoder-decoder based CNN, a U-Net CNN, a GAN with a PatchGAN discriminator, or other deep neural network, to generate the geometry of the 3D mesh, the computing systems provide process improvements by reducing iterations caused by defective or suboptimal dental appliances supplied to a dental practitioner when performing restorative treatment for a patient. In this way, the neural network-based dental appliance configuration techniques of this disclosure improve speed, accuracy, and predictability.

Restoring the patient's dental anatomy more quickly and/or more accurately may improve the functionality (e.g., reducing grinding or interference between teeth), which may improve the patient's quality of life, for example, by reducing pain caused by suboptimal dental morphology, integrity, or functioning. In some examples, restoring the patient's dental anatomy more accurately may improve the appearance of the patient's dental anatomy, which may further improve the patient experience and/or quality of life. Further, by creating a precise, quick, and predictable process for restoring dental anatomy by way of the neural network-formed geometry and/or placement, the computing systems of this disclosure provide efficiency enhancements for a wider range of dental practitioners and affordability improvements for a wider range of patients.

The details of one or more examples are set forth in the accompanying drawings and in the description below. Other features, objects, and advantages will be apparent from the description and drawings, and from the claims.

BRIEF DESCRIPTION OF THE DRAWINGS

FIG. 6 is a rendering illustrating an example center clip placement performed according to the neural network-based placement techniques of this disclosure.

FIG. 11A illustrates the input and output of a cGAN-trained generator network configured to generate a 2D image of a proposed dental anatomy using a 2D rendering of a current dental anatomy of a patient.

DETAILED DESCRIPTION

Figure 1:
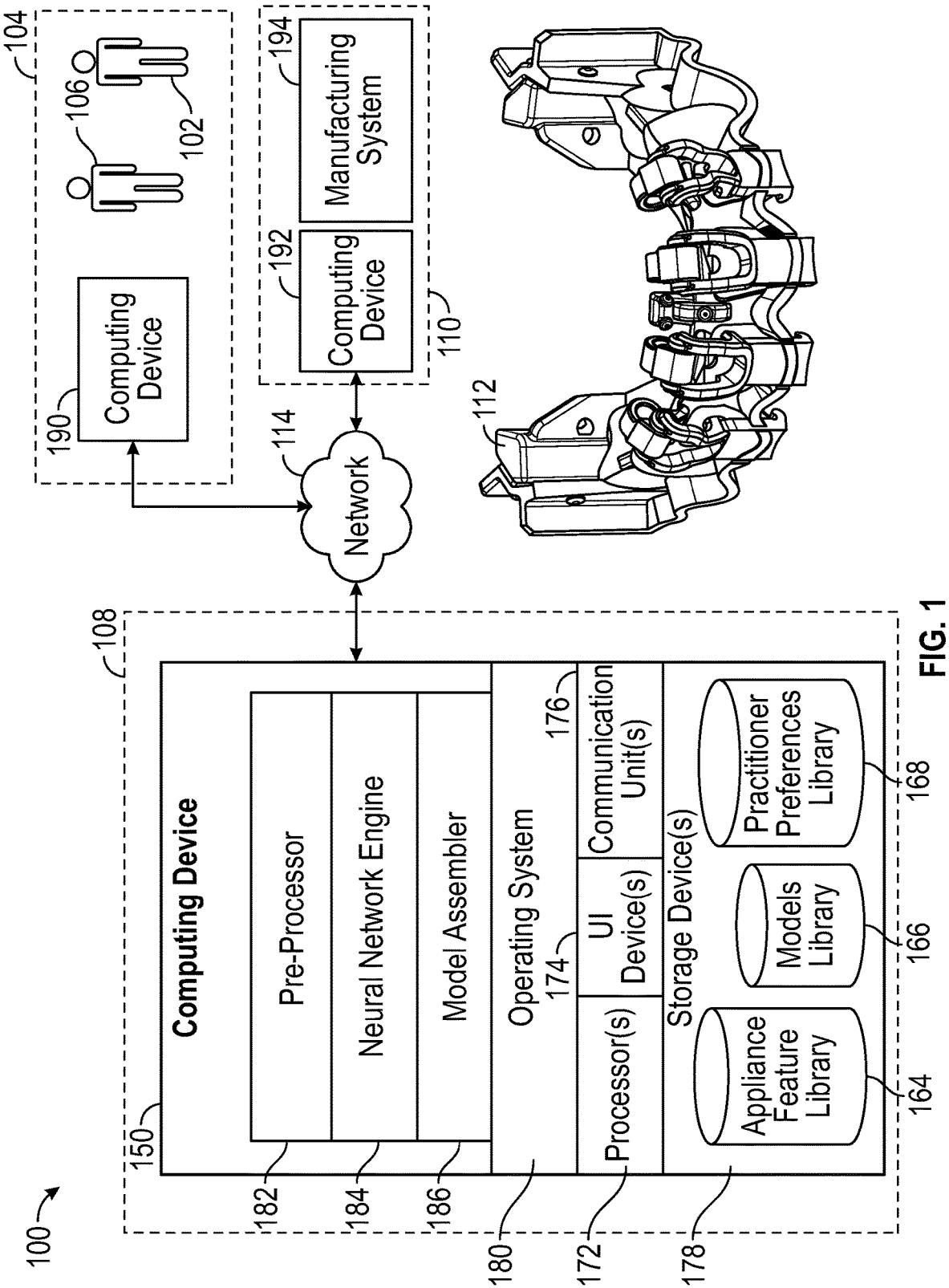
FIG. 1 is a block diagram illustrating an example system for designing and manufacturing a dental appliance for restoring the dental anatomy of a patient, in accordance with various aspects of this disclosure.

FIG. 1 is a block diagram illustrating an example system for designing and manufacturing a dental appliance for restoring the dental anatomy of a patient, in accordance with various aspects of this disclosure. In the example of FIG. 1, system 100 includes clinic 104, appliance design facility 108, and manufacturing facility 110.

Dental practitioner 106 may treat patient 102 at clinic 104. For example, dental practitioner 106 may create a digital model of the current dental anatomy of patient 102. The dental anatomy may include any portion of crowns or roots of one or more teeth of a dental archform, gingiva, periodontal ligaments, alveolar bone, cortical bone, bone grafts, implants, endodontic fillings, artificial crowns, bridges, veneers, dentures, orthodontic appliances, or any structure (natural or synthetic) that could be considered part of the dental anatomy of patient 102 before, during, or after treatment.

In one example, the digital model of the current dental anatomy includes a three-dimensional (3D) model of the current (pre-treatment) dental anatomy of patient 102. Clinic 104 may be equipped, in various examples, with an intra-oral scanner, cone beam computed tomography (CBCT) scanning (e.g., 3D X-ray) device, optical coherence tomography (OCT) device, magnetic resonance imaging (MRI) machine, or any other 3D image capturing system which dental practitioner 106 may utilize to generate the 3D model of the dental anatomy of patient 102.

In the example shown in FIG. 1, clinic 104 is equipped with computing system 190. Computing system 190 may represent a single device or a securely interconnected group of devices. In these examples, the individual devices of computing system 190 may form the secure interconnection by being entirely contained within the logical confines of clinic 104 (e.g., by way of physical connections within clinic 104, such as using a local area network or "LAN") and/or by way of virtual private network (VPN) tunneling-based encrypted communications securely communicated over a public network, such as the Internet. Computing system 190 may include one or more user-facing computing devices such as a personal computer (e.g., desktop computer, laptop computer, netbook, etc.), mobile device (e.g., tablet computer, smartphone, personal digital assistant, etc.), or any other electronic device configured to provide end-user computing capability, such as by presenting resources in a human-understandable form (e.g., visual images such as medical/dental imaging, legible output, symbolic/pictorial output, audible output, haptic output, etc.).

Dental practitioner 106 may store a digital model of the current dental anatomy of patient 102 to a storage device included in computing system 190 or is read/write accessible via computing system 190. In some examples, computing system 190 may also store a digital model of a proposed dental anatomy for patient 102. The proposed dental anatomy represents the intended function, integrity, and morphology of the dental anatomy to be achieved by application of a dental appliance 112 as part of dental restoration treatment of patient 102.

In one example, dental practitioner 106 may generate a physical model of the proposed dental anatomy and utilize an image capture system (e.g., as described above) to generate the digital model of the proposed dental anatomy. In another example, dental practitioner 106 may effectuate modifications to the digital model of the current anatomy of patient 102 (e.g., by adding material to a surface of one or more teeth of the dental anatomy, or in other ways) to generate the digital model of the proposed dental anatomy for patient 102. In yet another example, dental practitioner 106 may use computing system 190 to modify the digital model of the current dental anatomy of patient 102 to generate a model of the proposed dental anatomy for patient 102.

In one scenario, computing system 190 outputs the digital model(s) representing the current and/or proposed dental anatomies of patient 102 to another computing device, such as computing device 150 and/or computing device 192. Although described herein as being performed locally at computing systems 190, 150, and 192, it will be appreciated that, in some examples, one or more of computing systems 190, 150, and 192 may leverage cloud computing capabilities and/or software as a service (SaaS) capabilities to perform the underlying processing for the functionalities described herein. As illustrated in FIG. 1, in some examples, computing device 150 of design facility 108, computing system 190 of clinic 104, and computing device 192 of manufacturing facility 110 may be communicatively coupled to one another via network 114. Network 114 may, in various examples, represent or include a private network associated with an association (e.g., a dental services network, etc.) or other entity or grouping of entities.

In other examples, network 114 may represent or include a public network, such as the Internet. Although illustrated as a single entity in FIG. 1 purely for ease of illustration, it will be appreciated that network 114 may include a combination of multiple public and/or private networks. For instance, network 114 may represent a private network implemented using public network infrastructure, such as a VPN tunnel implemented over the Internet. As such, network 114 may comprise one or more of a wide area network (WAN) (e.g., the Internet), a LAN, a VPN, and/or another wired or wireless communication network. Network 114 may include a wired or wireless network components that conform to one or more standards, such as via Ethernet®, WiFi™, Bluetooth®, 3G, 4G LTE, 5G, and the like.

In the example of FIG. 1, computing device 150 is implemented by or at design facility 108. Computing device 150 is configured to automatically design a dental appliance and/or generate placement information for the dental appliance for reshaping the dental anatomy of patient 102. Computing device 150 (or components thereof) implement neural network technology to determine the geometry of and/or placement information for a dental appliance. In the example shown in FIG. 1, computing device 150 includes one or more processors 172, one or more user interface (UI) devices 174, one or more communication units 176, and one or more storage devices 178.

UI device(s) 174 may be configured to receive input data from a user of computing device 150 and/or provide output data to a user of computing device 150. One or more input components of UI devices 174 may receive input. Examples of input are tactile, audio, kinetic, and optical input, to name only a few examples. For example, UI devices 174 may include one or more of a mouse, keyboard, a voice input system, image capture devices (e.g., still camera and/or video camera hardware), physical or logical buttons, a control pad, a microphone or microphone array, or any other type of device for detecting input from a human user or another machine. In some examples, UI devices 174 may include one or more presence-sensitive input components, such as resistive screens, capacitive screens, single or multi-finger touchscreens, stylus-sensitive screens, etc.

Output components of UI device 174 may output one or more of visual (e.g., symbolic/pictorial or legible) data, tactile feedback, audio output data, or any other output data that is intelligible to a human user or to another machine. Output components of UI device 174, in various examples, include one or more of a display device (e.g., a liquid crystal display (LCD) display, touchscreen, stylus-sensitive screen, a light-emitting diode (LED) display, an optical head-mounted display (HMD), among others), a loudspeaker or loudspeaker array, a headphone or headphone set, or any other type of device capable of generating output data in a human or machine intelligible format.

Processor(s) 172 represent one or more types of processing hardware (e.g., processing circuitry), such as general-purpose microprocessor(s), specially designed processor(s), an application specific integrated circuit (ASIC), a field programmable gate array (FPGA), a collection of discrete logic, fixed function circuitry, programmable circuitry (or a combination of fixed function circuitry and programmable circuitry) or any type of processing hardware capable of executing instructions to perform the techniques described herein.

For example, storage device(s) 178 may store program instructions (e.g., software instructions or modules) that are executed by processor(s) 172 to carry out the techniques described herein. In other examples, the techniques may be executed by specifically programmed circuitry of processor 172 (e.g., in the case of fixed function circuitry or specifically programmed programmable circuitry). In these or other ways, processor(s) 172 may be configured to execute the techniques described herein, sometimes by leveraging instructions and other data accessible from storage device(s) 178.

Storage device(s) 178 may store data for processing by processor(s) 172. Certain portions of storage device(s) 178 represent a temporary memory, meaning that a primary purpose of these portions of storage device(s) 178 is not long-term storage. Short-term storage aspects of storage device(s) 178 may include volatile memory that is not configured to retain stored contents if deactivated and reactivated (e.g., as in the case of a power-cycle). Examples of volatile memories include random access memories (RAM), dynamic random access memories (DRAM), static random access memories (SRAM), and other forms of volatile memories known in the art. In some examples, short-term memory (e.g., RAM) of storage device(s) 178 may include on-chip memory unit(s) collocated with portions of processor(s) 172 to form a portion of an integrated circuit (IC) or a portion of a system on a chip (SoC).

Storage device(s) 178 may, in some examples, also include one or more computer-readable storage media. Storage device(s) 178 may be configured to store larger amounts of data than volatile memory. Storage device(s) 178 may further be configured for long-term storage of data as non-volatile memory space and retain data after activate/off cycles. Examples of nonvolatile memories include, solid state drives (SSDs), hard disk drives (HDDs), flash memories, or forms of electrically programmable memories (EPROM) or electrically erasable and programmable (EEPROM) memories. Storage device(s) 178 may store program instructions and/or data associated with software components and/or operating systems of computing device 150.

In the example of FIG. 1, storage device(s) 178 include appliance feature library 164, models library 166, and practitioner preferences library 168 (collectively, "libraries 164-168). Libraries 164-168 may include relational databases, multi-dimensional databases, maps, hash tables, or any other data structure. In one example, models library 166 includes 3D models of the patient's current and/or proposed dental anatomy. In some instances, libraries 164-168 may be stored locally at computing device 150 or may be accessed via a networked file share, cloud storage, or other remote datastore accessible using network interface hardware of communication unit(s) 176.

Short-term memory of storage device(s) 178 and processor(s) 172 may collectively provide a computing platform for executing operating system 180. Operating system 180 may represent an embedded, real-time multitasking operating system, for instance, or may represent any other type of operating system. Operating system 180 provides a multitasking operating environment for executing one or more software components 182-186. In some examples, operating system 180 may execute any of components 182-188 as an instance of a virtual machine or within a virtual machine instance executing on underlying hardware. Although illustrated separately from operating system 180 as a non-limiting example, it will be appreciated that any of components 182-188 may be implemented as part of operating system 180 in other examples.

In accordance with the techniques of this disclosure, computing device 150 automatically or semi-automatically generates a digital model of dental appliance 112 for restoring the dental anatomy of patient 102 using one or more types of neural networks trained with dental anatomy-related data and/or appliance feature data pertaining to patient 102 and/or other (actual or hypothetical) patients. Pre-processor 182 is configured to pre-process the digital model of the proposed dental anatomy of patient 102.

In one example, pre-processor 182 performs pre-processing to identify one or more teeth in the proposed dental anatomy of patient 102. In some instances, pre-processor 182 identify a local coordinate system for each individual tooth and may identify a global coordinate system that includes each tooth of the proposed dental anatomy (e.g. in one or both arches of the proposed dental anatomy). As another example, pre-processor 182 may pre-process the digital model of the proposed dental anatomy to identify the root structure of the dental anatomy.

In another example, pre-processor 182 may identify the gingiva of the gums in the proposed dental anatomy, thereby identifying and delineating portions of the proposed dental anatomy that include gingiva and portions of the proposed dental anatomy that include tooth. As yet another example, pre-processor 182 may pre-process the digital model of the proposed dental anatomy by extending the roots to identify the top surface of the root of each respective tooth. Pre-processor 182 may perform one, several, or all of the various example functionalities described above, in various use case scenarios, depending on requests provided by dental practitioner 106, based on data availability with respect to patient 102 and/or other patient(s), and potentially depending on other factors.

Computing device 150 (or hardware/firmware components thereof) may invoke or activate neural network engine 184 to determine placement information of dental appliance 112 during dental restorative treatment of patient 102. In some examples, neural network engine 184 may implement a two-hidden-layer neural network trained with placement information for patient 102 and/or for other patients with generally corresponding dental anatomies (current or proposed).

In these examples, neural network engine 184 may implement the neural network to accept, as inputs, individual position/orientation information for each of two teeth (e.g., a pair of adjacent teeth) in the current dental anatomy of patient 102, and may output placement information for dental appliance 112 during dental restorative therapy. For instance, the placement information may directly or indirectly reflect one or more of the position, orientation, or sizing of dental appliance 112 as it is to be used in the dental restorative treatment of patient 102.

In one example, neural network engine 184 may train the neural network using a backpropagation algorithm using a single 4×4 transform for each of the two adjacent teeth, and another 4×4 transform that identifies a "ground truth" {position, orientation, size} tuple of dental appliance 112 after placement is completed as part of the dental restoration treatment of patient 102. As used herein, the term "transform" refers to change (or "delta") information with respect to the {position, orientation, size} tuple, and can therefore also be described as a {translation, rotation, scale} tuple with respect to dental appliance 112.

In some instances, the transforms of this disclosure may include additional elements as well, such as a shear mapping (or simply "shear") associated with dental appliance 112. As such, the transforms of this disclosure may, in various examples, represent affine transforms, and may include some or all transformations included in the possible transformations under the automorphism in an affine space.

Neural network engine 184 may extract the transforms for the specific teeth from 3D mesh data describing the current and/or proposed dental anatomy of patient 102. As used herein, the term "ground truth" refers to a proven or otherwise well-founded description of dental anatomy features or appliance features. As such, in some examples, a ground truth transform may be produced manually by dental practitioner 106 or a technician using a CAD tool.

In other examples, a ground truth transform may be generated automatically, such as by using the automated techniques described in WO 2020/240351, filed May 20, 2020, the entire content of which is incorporated herein by reference. Various techniques of this disclosure are described below with respect to the non-limiting example of positioning, orienting, and sizing of a center clip that is placed over the gap between two adjacent teeth during dental restoration. It will be appreciated, however, that neural network engine 184 may implement the techniques of this disclosure to generate geometries and/or placement information for other types of dental appliances, as well.

As part of generating the placement information for a center clip, neural network engine 184 may identify landmarks of the proposed dental anatomy. Example landmarks include a slice, a midpoint, a gingival boundary, a closest point between two adjacent teeth (e.g., a point of contact between adjacent teeth or a point of closest approach (or closest proximity), a convex hull, a center of mass, or other landmark. A slice refers to a cross section of the dental anatomy. The midpoint of a tooth refers to a geometric center (also referred to as a geometrical midpoint) of the tooth within a given slice.

The gingival boundary refers to a boundary between the gingiva and one or more teeth of a dental anatomy. A convex hull refers to a polygon, the vertices of which include a subset of the vertices in a given set of vertices, where the boundary of the subset of vertices circumscribes the entire set of vertices. The center of mass of a tooth refers to a midpoint, center point, centroid, or geometric center of the tooth. In some instances, neural network engine 184 may determine one or more of these landmarks as expressed using a local coordinate system for each tooth.

In some examples, as part of landmark identification, neural network engine 184 determines a plurality of slices of the patient's proposed dental anatomy. In one example, the thickness of each slice is the same. In some instances, the thickness of one or more slices is different than the thickness of another slice. The thickness of a given slice may be pre-defined. In one instance, neural network engine 184 automatically determines the thickness of each slice using the simplified neural network of this disclosure. In another instance, the thickness of each slice may be user-defined and, for example, available as a ground truth input to the simplified neural network.

As part of landmark identification, neural network engine 184 may, in some examples, determine a midpoint for each tooth to which the placement of dental appliance 112 pertains. In one example, neural network engine 184 identifies a landmark using a midpoint of a particular tooth by computing the extrema of that particular tooth's geometry based on the entirety of that particular tooth (e.g., without dividing the dental anatomy into slices) and determining the midpoint of that particular tooth based on the extrema of the tooth geometry.

In some examples, neural network engine 184 may determine a midpoint for each tooth for each slice. For instance, neural network engine 184 may determine the midpoint for a particular slice of a particular tooth by calculating the center of mass of a constellation of vertices around the edge of the particular tooth for that particular slice. In some instances, the midpoint of the particular tooth for the particular slice may be biased toward one edge of the tooth (e.g. in the case that one edge has more points than another edge).

In other examples, neural network engine 184 may, as part of the landmark identification portion of the placement generation, determine the midpoint of a particular tooth in a particular slice based on a convex hull of the particular tooth for the particular slice. For example, neural network engine 184 may determine a convex hull of a set of edge points of the tooth for a given slice. In some instances, neural network engine 184 executes a neural network that, as part of landmark identification, determines a geometric center from the convex hull by performing a flood-fill operation on the region circumscribed by the convex hull and computing a center of mass of the flood-filled convex hull.

In some examples, the neural network executed by neural network engine 184 outputs a closest point between two adjacent teeth. The closest point between two adjacent teeth may be a point of contact or a point of closest approach. In one example, neural network engine 184 determines a closest point between two adjacent teeth for each slice. In another example, neural network engine 184 determines a closest point between two adjacent teeth based on the entirety of the adjacent teeth (e.g., without dividing the dental anatomy into slices).

Using landmarks computed for the proposed dental anatomy, the neural network executed by neural network engine 184 generates one or more custom appliance features for dental appliance 112 based at least in part on the landmarks. For example, custom feature generator 184 may generate the custom appliance features by determining the characteristics of the custom appliance features, such as a size, shape, position, and/or orientation of the custom appliance features. Examples of custom appliance features include a spline, a mold parting surface, a gingival trim surface, a shell, a facial ribbon, a lingual shelf (also referred to as a "stiffening rib"), a door, a window, an incisal ridge, a case frame sparing, a diastema matrix wrapping, among others.

In some examples, neutral network engine 184 may identify and use features other than the examples listed above. For example, neural network engine 184 may identify and use features that are discernible and actionable to processor(s) 172 within the mathematical framework of the executed neural network. As such, the operations performed via the neural network executed by neural network engine 184 may represent a "black box" in terms of the features used and the mathematical framework applied by the neural network during execution.

A spline refers to a curve that passes through a plurality of points or vertices, such as a piecewise polynomial parametric curve. A mold parting surface refers to a 3D mesh that bisects two sides of one or more teeth (e.g., separates the facial side of one or more teeth from the lingual side of the one or more teeth). A gingival trim surface refers to a 3D mesh that trims an encompassing shell along the gingival margin. A shell refers to a body of nominal thickness. In some examples, an inner surface of the shell matches the surface of the dental arch and an outer surface of the shell is a nominal offset of the inner surface.

The facial ribbon refers to a stiffening rib of nominal thickness that is offset facially from the shell. A window refers to an aperture that provides access to the tooth surface so that dental composite can be placed on the tooth. A door refers to a structure that covers the window. An incisal ridge provides reinforcement at the incisal edge of dental appliance 112 and may be derived from the archform. The case frame sparing refers to connective material that couples parts of dental appliance 112 (e.g., the lingual portion of dental appliance 112, the facial portion of dental appliance 112, and subcomponents thereof) to the manufacturing case frame. In this way, the case frame sparing may tie the parts of dental appliance 112 to the case frame during manufacturing, protect the various parts from damage or loss, and/or reduce the risk of mixing-up parts.

In some examples, the neural network executed by neural network engine 184 generates one or more splines based on the landmarks. The neural network executed by neural network engine 184 may generate a spline based on a plurality of tooth midpoints and/or closest points between adjacent teeth (e.g., points of contact between adjacent teeth or points of closest proximity between adjacent teeth). In some instances, the neural network executed by neural network engine 184 generates one spline for each slice. In one instance, neural network engine 184 generates a plurality of splines for a given slice. For instance, neural network engine 184 may generate a first spline for a first subset of teeth (e.g., right posterior teeth), a second spline for a second subset of teeth (e.g., left posterior teeth), and a third spline for a third subset of teeth (e.g., anterior teeth).

Neural network engine 184 generates, in some scenarios, a mold parting surface based on the landmarks. The mold parting surface may be used to split an encompassing shell for molding without undercuts. In some examples, neural network engine 184 generates additional copies of the mold parting surface. For example, the neural network executed by neural network engine 184 may place one or more copies of a mold parting surface at small offsets to the main parting surface for the purpose of creating an interference condition when the appliance is assembled (which may, for example, improve shape adaptation and sealing when applying a tooth restoration material to the teeth).

Appliance feature library 164 includes a set of pre-defined appliance features that may be included in dental appliance 112. Appliance feature library 164 may include a set of pre-defined appliance features that define one or more functional characteristics of dental appliance 112. Examples of pre-defined appliance features include vents, rear snap clamps, door hinges, door snaps, an incisal registration feature, center clips, custom labels, a manufacturing case frame, a diastema matrix handle, among others. Each vent is configured to enable excess dental composite to flow out of dental appliance 112.

Rear snap clamps are configured to couple a facial portion of dental appliance 112 with a lingual portion of dental appliance 112. Each door hinge is configured to pivotably couple a respective door to dental appliance 112. Each door snap is configured to secure a respective door in a closed position. In some examples, an incisal registration feature comprises a male and female tab pair that falls on the incisal edge of dental appliance 112 (e.g., along the midsagittal plane). In one example, the incisal registration feature is used to maintain vertical alignment of a facial portion of dental appliance 112 and a lingual portion of dental appliance 112.

Each center clip is configured to provide vertical registration between the lingual portion of dental appliance 112 and the facial portion of dental appliance 112. Each custom label includes data identifying a part of dental appliance 112. The manufacturing case frame is configured to support one or more parts of dental appliance 112. For example, the manufacturing case frame may detachably couple a lingual portion of dental appliance 112 and a facial portion of dental appliance 112 to one another for safe handling and transportation of dental appliance 112 from manufacturing facility 110 to clinic 104.

The neural network executed by neural network engine 184 may, in some examples, determine the characteristics of one or more pre-defined appliance features that are included in pre-defined appliance feature library 164. For instance, one or more features accessible from predefined appliance feature library 164 may represent component shapes obtained in one or more ways, such as by way of manual generation (e.g., by dental practitioner 106 or via automated generation, such as via the techniques described in WO 2020/240351, filed May 20, 2020 described above). Based on availability and pertinence to the current dental anatomy of patient 106, the neural network may be trained (at least partially) using the information available from pre-defined appliance feature library 164.

In one example, the pre-defined appliance features are configured to enable or perform functionalities attributed to dental appliance 112. The characteristics of the pre-defined appliance features may include one or more of the transform-related attributes described above (e.g., position, orientation, size) and/or other attributes, such as shape information. The neural network executed by neural network engine 184 may determine the characteristics of the pre-defined appliance features based on one or more rules, such as rules that are generated and/or refined via machine learning (ML) techniques.

In some examples, the executed neural network determines placement information for a rear snap clamp based on the rules. In one example, neural network engine 184 may generate placement information that positions two rear snap clamps along one archform during dental restorative treatment, with the two rear snap clamps being disposed on opposite ends of the archform. For instance, a first snap clamp may be placed at one end of the archform during dental restorative treatment, and a second snap clamp may be placed at the other end of the same archform during the dental restorative treatment.

In some examples, neural network engine 184 may assign a position to one or both of the rear snap clamps one tooth beyond the outer-most teeth to be restored. In some examples, neural network engine 184 positions a female portion of the rear snap clamp on the lingual side of the parting surface and position a male portion of the rear snap clamp on the facial side may. In some examples, neural network engine 184 determines placement information for a vent during dental restorative treatment, based on the rules. For example, neural network engine 184 may assign the vent a position at the midline of a corresponding door on an incisal side of dental appliance 112.

In some scenarios, neural network engine 184 determines a placement of a door hinge based on the rules. In one scenario, neural network engine 184 assigns each door hinge a position at the respective midline of a corresponding door. In one scenario, neural network engine 184 determines a positioning in which the female portion of the door hinge is anchored to the facial portion of dental appliance 112 (e.g., towards the incisal edge of a tooth) and positions the male portion of the door hinge to anchor to the outer face of the door.

In one instance, neural network engine 184 determines a placement of a door snap based on the rules by positioning the door snap along a midline of a corresponding door. In one instance, neural network engine 184 determines a positioning which the female portion of the door snap anchors to an outer face of the door and extends downward toward the gingiva. In another instance, neural network engine 184 determines a position according to which the male portion of the door snap is anchored to the gingival side of the facial ribbon. For example, the door snap may secure the door in a closed position by latching the male portion of the door snap to the facial ribbon.

Neural network engine 184 may determine the characteristics of a pre-defined appliance feature based on preferences of dental practitioner 106. Practitioner preferences library 168 may include data indicative of one or more preferences of dental practitioner 106. As such, neural network engine 184 may use information from practitioner preferences library 168 that pertains to dental practitioner 106 as training data in the overall training of the neural network being executed to determine placement or geometry information for dental appliance 112.

Practitioner preferences may, in various use case scenarios, directly affect the characteristics of one or more appliance features of dental appliance 112. For example, practitioner preferences library 168 may include data indicating a preferred size of various appliance features, such as the size of the vents. In some such examples, larger vents may enable the pressure of the dental composite or resin to reach equilibration faster during the filling process but may result in a larger nub to finish after curing. In these examples, neural network engine 184 may train the neural network with scaling information that sizes dental appliance 112 according to the preference attributed to dental practitioner 106.

In other examples, practitioner preferences indirectly affect the characteristics of appliance features. For example, practitioner preferences library 168 may include data indicating a preferred stiffness of the appliance or a preferred tightness of a self-clamping feature. Such preference selections may also affect more complex design changes to section thickness of the matrix and or degree of activation of the clamping geometry. Neural network engine 184 may determine the characteristics of the appliance features by augmenting the rules upon which the implemented neural network is trained using preferences of dental practitioner 106 (or other dental practitioners, in some cases) available from practitioner preferences library 168. In some examples, neural network engine 184 may augment the rules with the practitioner preference data based on a simulation (e.g. Monte Carlo) or finite element analysis performed using the practitioner preference information. In some instances, feature characteristics also may be derived from properties in the materials to used with the matrix, such as type of composite that the dentist prefers to use with the appliance.

Using the outputs of the neural network executed by neural network engine 184, model assembler 186 generates a digital 3D model of dental appliance 112 used to re-shape the dental anatomy (e.g., form the current dental anatomy to the proposed dental anatomy) of patient 102. In various examples, model assembler 186 may generate the digital 3D model using custom and/or pre-defined appliance features that form the outputs of the neural network executed by neural network engine 184. The digital 3D model of dental appliance 112 may include, be, or be part of one or more of a point cloud, 3D mesh, or other digital representation of dental appliance 112. In some instances, model assembler 186 stores the digital model of dental appliance 112 in models library 166.

Model assembler 186 may output the digital model of dental appliance 112 in various ways. In one example, model assembler 186 may output the digital 3D model of dental appliance 112 to computing device 192 of manufacturing facility 110 (e.g., via network 114 using network interface hardware of communication unit(s) 176). By providing the digital 3D model to computing device 192, model assembler 186 may enable one or more entities at manufacturing facility 110 to manufacture dental appliance 112. In other examples, computing device 150 may send the digital model of dental appliance 112 to computing system 190 of clinic 104. In these examples, model assembler 186 may enable dental practitioner 106 or other entities at clinic 104 to manufacture dental appliance 112 onsite at clinic 104.

In some examples, computing device 192 may invoke network interface hardware of communication unit(s) 176 to send the digital 3D model of dental appliance 112 to manufacturing system 194 via network 114. In these examples, manufacturing system 194 manufactures dental appliance 112 according to the digital 3D model of dental appliance 112 formed by model assembler 186. Manufacturing system 194 may form dental appliance 112 using any number of manufacturing techniques, such as 3D printing, chemical vapor deposition (CVD), thermoforming, injection molding, lost wax casting, milling, machining, or laser cutting, among others.

Dental practitioner 106 may receive dental appliance 112 and may utilize dental appliance 112 to re-shape one or more teeth of patient 102. For example, dental practitioner 106 may apply a dental composite to the surface of one or more teeth of patient 102 via one or more doors of dental appliance 112. Dental practitioner 106 or another clinician at clinic 104 may remove excess dental composite via one or more vents.

In some examples, model assembler 186 may store the generate digital 3D model of dental appliance 112 to models library 166. In these examples, models library 166 may provide appliance model heuristics that neural network engine 184 may use as training data in training one or more neural networks. In some examples, models library 166 includes data indicative of appliance success criteria associated with each completed instance of dental appliance 112. Neural network engine 184 may augment the neural network training datasets with any appliance success criteria available from models library 166. The appliance success criteria may indicate one or more of a manufacturing print yield, practitioner feedback, patient feedback, customer feedback or ratings, or a combination thereof.

For example, neural network 184 may train the neural network to generate a new or updated placement profile and/or geometry of dental appliance 112 via the digital 3D model using the appliance success criteria determined for previously generated dental appliances. The neural network executed by neural network engine 184 may, as part of the training, determine whether the appliance success criteria meet one or more threshold criteria, such as one or more of a threshold manufacturing yield, a threshold practitioner-provided rating, a threshold patient satisfaction rating, etc.

In one example, the existing digital 3D model available from models library 166 is a template or reference digital model. In such examples, neural network engine 184 may train the neural network partly based on the template digital model. The template digital model may, in various examples, be associated with different characteristics of the current dental anatomy of patient 102, such as a template for patients having small teeth or impediments to opening the mouth beyond a certain width.

In one example, neural network engine 184 trains the neural network using previously generated digital 3D models available from models library 166. For example, neural network engine 184 utilize one or more morphing algorithms to adapt the previously generated digital 3D models accessed from models library 166 to the situation represented by the dental restorative treatment being tailored to the dentition of patient 102 during training and/or execution of the neural network.

For example, neural network engine 184 may utilize morphing algorithms to interpolate appliance feature geometries, and/or may generate a new digital model of a dental appliance 112 based on the design of the existing digital model. In one instance, the design feature of an existing digital model may include a window inset from the perimeter, such that neural network engine 184 may morph the geometry of the existing digital model based on landmarks for a different dental anatomy.

Neural network engine 184 trains and executes the neural network to perform (and potentially, compress) multiple intermediate steps in the process of generating a digital 3D model of dental appliance 112 for placement and geometry purposes. Neural network engine 184 generates the feature set describing dental appliance 112 using 3D meshes of the current and/or proposed dental anatomy of patient 102. The 3D meshes (or "tooth meshes") and, in examples where available, library components, form training inputs to the neural network.

As described above, neural network engine 184 may train the neural network to automate one or both of component placement and/or geometry generation for components of dental appliance 112. Examples of components include a center clip registration tab (or "beak"), door hinges, door snaps, door vents, rear snap clamps, and various others. Examples of placement-related factors and/or components that neural network engine 184 may generate include a parting surface, a gingival trim, doors, windows, facial ribbon, incisal ridge, lingual shelf, diastema matrix, case frame, part label(s), etc.

Neural network engine 184 implements the neural network to automate placement information generation and/or geometry-generation operations for components such as door hinges and center clips, must be placed in specific positions relative to 3D representations of the teeth of the dental anatomy of patient 102 to perform dental restoration. By leveraging neural network technology to automate the placement and/or geometry information of these components, significantly reduces the process turnaround for using dental appliance 112 during dental restorative therapy of patient 102.

Also, by leveraging a neural network trained with the combination of datasets set forth in this disclosure, neural network engine 184 automates the placement and/or geometry generation with improved consistency and precision, such as by updating the training of the neural network based on ongoing feedback information or other dynamically changing factors.

The neural network-based automated algorithms of this disclosure implemented by computing device 150 provide several advantages in the form of technical improvements in the technical field of restorative dental appliance configuration. As one example, computing device 150 may invoke neural network engine 184 to generate placement and/or geometry information for dental appliance 112 without the need to explicitly compute tooth geometry landmarks at each instance.

Instead, neural network engine 184 may execute a neural network trained with the various transform data and/or ground truth data described above to generate the placement and/or geometry information based on these training factors. As another example, computing device 150 may improve the data precision associated with the digital 3D model of dental appliance 112 by continuously improving the output of the neural network based on treatment plans and results from previous patients, feedback from dental practitioner 106 and/or patient 102, and other factors that can be used to fine tune the neural network using ML techniques.

As another example, because neural network engine 184 may implement further refinements to the algorithms through introducing new training data rather than modifying rules-based logic, the techniques of this disclosure may provide reusability and compute resource sustainability improvements, as well. While described primarily with respect to appliances used in dental restorative therapy as an example, it will be appreciated that neural network engine 184 may, in other examples, be configured to implement algorithms of this disclosure to generate geometry and/or placement information for other types of dental appliances as well, such as orthodontic equipment, surgical guides, and bracket bonding templates, etc.

While computing device 150 is described herein as performing both the training and execution of the various neural networks of this disclosure, it will be appreciated that, in various use case scenarios, the training of the neural networks may be performed by devices or systems that are separate from the devices that execute the trained neural networks. For instance, a training system may use some or all of the training data described with respect to FIG. 1, in the form of labeled training datasets, to form one or more trained models. Other devices may import the trained model(s), and execute the trained model(s) to produce various neural network output(s) described above.

Figure 2:
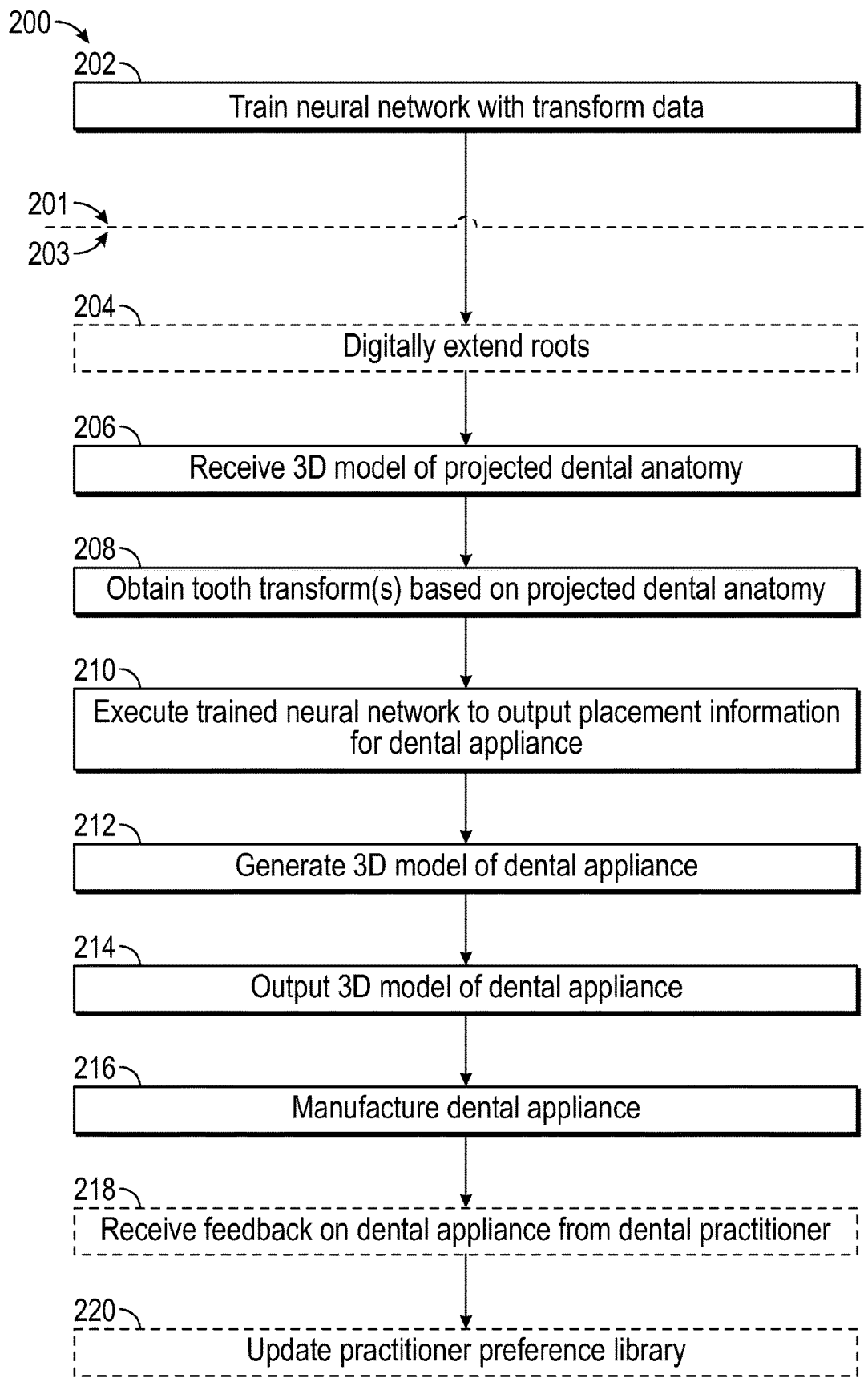
FIG. 2 is a flowchart illustrating an example process that the system of FIG. 1 may perform to generate a digital model of a dental appliance by executing a neural network trained according to aspects of this disclosure.

FIG. 2 is a flowchart illustrating an example process 200 that system 100 may perform to generate a digital model of a dental appliance by executing a neural network trained according to aspects of this disclosure. Process 200 may begin with training phase 201. As part of training phase 201, neural network engine 184 may train the neural network using transform data associated with 3D models of various dental anatomies (202). According to various aspects of this disclosure, neural network engine 184 may train a neural network using backpropagation training techniques.

In some examples, neural network engine 184 may use one 4×4 transform for each of one or more teeth of the dental anatomy, and one 4×4 transform that defines the ground truth {position, orientation, size} tuple for dental appliance 112 after placement is completed. In the example of dental appliance 112 representing a center clip, neural network engine 184 may extract the transforms for the pair of maxillary central incisors (denoted as teeth "8 and 9" in the universal notation system for permanent teeth) or the pair of mandibular central incisors (denoted as teeth "24 and 25" in the universal notation system for permanent teeth) from the 3D mesh data describing the proposed dentition of patient 102.

The ground truth transform may represent "pristine" data that is produced manually by a technician using computer-aided design (CAD) tool to position and orient the center clip, or alternatively, may represent pristine data produced automatically in various ways, such as by using the automated techniques described in WO 2020/240351, filed May 20, 2020. By training the neural network using the backpropagation algorithm, neural network engine 184 generates multiple layers that are fully connected. That is, a weighted connection exists between a given node in a first layer and each of respective node in the next layer.

The backpropagation algorithm implemented by neural network engine 184 adjusts the weights for these inter-layer node-to-node connections through the course of training the neural network, thereby gradually encoding the desired logic into the neural network over the course of multiple training iterations or passes. In some examples of this disclosure, the neural network may include two layers, thereby mitigating computational overhead with respect to both training and eventual execution.

While described herein with respect to training the neural network with transforms for two teeth using data from one or more past cases, it will be appreciated that, in other examples, neural network engine 184 may train the neural network with different types and/or quantities of training data as well. The augmentation of training data may depend on the availability and accessibility of such training data. For example, if accessible from models library 166 or from another source, neural network engine 184 may augment the training data with which to train the neural network using transforms for other teeth of the archform to which dental appliance 112 is to be applied, and/or using transforms for one or more teeth of the opposing archform.

In this way, neural network engine 184 may train the neural network using training data that enables the neural network to determine positioning information for dental appliance 112 based on a more holistic evaluation of the dental anatomy of patient 102. In these and/or other examples, neural network engine 184 may augment the training data with pertinent preference information available from practitioner preferences library 168, with patient feedback information, and/or with various other pertinent data that is accessible to computing device 150.

After completing training phase 201 of process 200, neural network engine 184 may commence execution phase 203. Execution phase 203 may begin when computing device 150 receives a digital 3D model of a proposed (e.g., post dental restoration therapy) dental anatomy for patient 102 (204). In one example, computing device 150 receives the digital 3D model of the proposed dental anatomy from another computing device, such as computing system 190 of clinic 104. The digital 3D model of the proposed dental anatomy for patient 102 may include a point cloud or 3D mesh of the proposed dental anatomy.

A point cloud includes a collection of points that represent or define an object in a 3D space. A 3D mesh includes a plurality of vertices (also referred to as points) and geometric faces (e.g., triangles) defined by the vertices. In one example, dental practitioner 106 generates a physical model of the proposed dental anatomy for patient 102, and utilizes an image capture system to generate the digital 3D model of the proposed dental anatomy from images captured of the physical model. In another example, dental practitioner 106 modifies a digital 3D model of the current dental anatomy of patient 102 (e.g., by simulating the addition of material to a surface of one or more teeth of the dental anatomy, or by simulating other changes) to generate the digital 3D model of the proposed dental anatomy. In yet another example, computing system 190 may modify the digital model of the current dental anatomy to generate a model of the proposed dental anatomy.

In some examples, pre-processor 182 pre-processes the 3D model of the proposed dental anatomy to generate a modified model by digitally extending the roots of the initial digital model of the proposed dental anatomy according to the proposed root extension determined by pre-processor 182, thereby more accurately modeling the complete anatomy of the patient's teeth (206). Step 206 is illustrated in FIG. 2 using a dashed-line border, to indicate the optional nature of step 206. For example, the pre-processing functionalities provided by step 206 may, in some use case scenarios, be subsumed by the functionalities described herein with respect to neural network engine 184.

In some examples in which pre-processor 182 performs step 206, because the tops (e.g., the area furthest from the gingival emergence) of the roots may be at different heights, pre-processor 182 may detect the vertices corresponding to the tops of the roots and then project those vertices along a normal vector, thereby digitally extending the roots. In one example, preprocessor 182 groups vertices into clusters (e.g., using a k-means algorithm). Pre-processor 182 may compute the average normal vector for each cluster of vertices.

For each cluster of vertices, pre-processor 182 may determine a sum of residual angular differences between the average normal vector for the cluster and the vector associated with each of the vertices in the cluster. In one example, pre-processor 182 determines which cluster of vertices is the top surface of the roots based on the sum of the residual angular differences for each cluster. For example, pre-processor 182 may determine that the cluster with the lowest sum of residual angular differences defines the top surface of the roots.

Neural network engine 184 may obtain one or more tooth transforms based on the proposed dental anatomy represented in the received 3D model (208). For example, neural network engine 184 may extract respective {translation, rotation, scaling} tuples for one or more teeth represented in the 3D model based on corresponding {position, orientation, size} tuples for the teeth in the current dental anatomy and dental restoration outcome information shown in the 3D model of the proposed (post-restoration) dental anatomy for patient 102.

Neural network engine 184 may execute the trained neural network to output placement information for dental appliance 112 (210). In the example of dental appliance 112 representing a center clip, neural network 184 may input two teeth transforms (e.g. transforms describing the positions, orientations, and dimensionality of the two adjacent maxillary central incisors) to the neural network with two layers described above. The neural network executed by neural network 184 may output a transform that positions the center clip (which may represent a library part) between the two maxillary central incisors, and oriented normal to the overall archform of a current, intermediate, or proposed dental anatomy of patient 102.

Neural network engine 184 may generate the transform for dental appliance 112 as applied to the dental restorative treatment of patient 102 (the output of the trained neural network upon execution) using various underlying operation sets. As one example, the trained neural network may process the 3D model of the proposed dental anatomy of patient 102 to automatically detect a set of one or more landmarks of the proposed dental anatomy. In this example, each "landmark" represents an identifiable geometric construct within the 3D model that is useful for determining the position and orientation with respect to one or more tooth surfaces. In some examples, the landmarks computed by the trained neural network include one or more slices of the dental anatomy, where each slice may include one or more additional landmarks. For example, the trained neural network may divide the 3D mesh of the proposed dental anatomy into multiple slices, and may compute one or more landmarks for each slice, such as a midpoint for each tooth in the slice, a closest point between two adjacent teeth (e.g., a point of contact between two adjacent teeth or a point of closest approach between two adjacent teeth), a convex hull for each tooth in the slice, among others.

Model assembler 186 generates a 3D model of dental appliance 112 (212). In various examples of this disclosure, model assembler 186 may construct an overall 3D mesh for dental appliance 112 based on placement information indicated by the transform output by the neural network executed by neural network engine 184. For example, model assembler 186 may generate the overall 3D mesh for dental appliance 112 based on one or more of the placement characteristics indicated by the {translation, rotation, scale} tuple of a transform of this disclosure.

In some examples, model assembler 186 may also factor shear or shear mapping information for dental appliance 112 into the output transform, if shear information is available for the input data to the executed neural network and/or if neural network engine 184 otherwise generates shear information for dental appliance 112 by executing the trained model of the neural network.

In one example, model assembler 186 may extrapolate (e.g., via integration or other similar techniques) one or more characteristics of a {position, orientation, size} tuple for dental appliance 112 from the transform output by the neural network. The {position, orientation, size} tuple of each 3D mesh generated by model assembler 186 corresponds to a set of appliance features (e.g., one or both of custom and/or pre-defined appliance features) for the proposed overall structure of dental appliance 112. In one example, model assembler 186 may determine the position of a custom appliance feature based on the midpoint of a particular tooth.

For example, modeler assembler 186 may align or otherwise position a 3D mesh of a window and/or door (as example features) based on a midpoint of the tooth. In this way, model assembler 186 may determine the position of a pre-defined appliance feature based on the transform information output by the neural network executed by neural network engine 184. As one example, model assembler 186 may determine the position of a rear snap clamp based on the position of the teeth in the current dental anatomy of patient 102.

In some instances, model assembler 186 determines the position of a pre-defined appliance feature based on the position of a custom appliance feature. For instance, modeler assembler 186 may align a door hinge, door snap, and/or vent with a midline of a door. Further, the model assembler 186 may adjust the feature orientation, scale, or position based on analysis of the overall model, such as performing a finite element analysis to adjust the active clamping forces of snap clamp. Model assembler 186 may also make adjustments (e.g. to fine tune) based on subsequent expected manufacturing tolerances, such as providing suitable clearance between features.

Similarly, model assembler 186 may make adjustments based on the properties of the material used in the creation of the physical appliance, such as increasing thicknesses when using more flexible materials. In various examples in accordance with this aspects of this disclosure, model assembler 186 may generate the digital 3D model of dental appliance 112 to include one or more of a point cloud, a 3D mesh, or other digital representation(s) of dental appliance 112.

Computing device 150 outputs the digital 3D model of dental appliance 112 (214). For example, computing device 150 may output the digital 3D model of dental appliance 112 to computing device 192 of manufacturing facility 110 by invoking network interface hardware of communication unit(s) 176 to transmit packetized data over network 114. Manufacturing system 194 manufactures dental appliance 112 (216). For instance, computing device 192 may control manufacturing system 194 to fabricate dental appliance 112 such that it complies with the placement information generated by the trained neural network executed by neural network engine 184 (e.g., based on the digital 3D model of dental appliance 112 generated by model assembler 186). In various examples, manufacturing system 194 may generate the physical dental appliance 112 via 3D printing, CVD, machining, milling, or any other suitable technique.

In some examples, computing system 150 receives feedback on dental appliance 112 from dental practitioner 106 (218). The optional nature of step 218 is illustrated in FIG. 2 by way of dashed-line borders. For example, after dental practitioner 106 receives the physical dental appliance 112 and uses it for dental restorative treatment of patient 102, dental practitioner 106 may utilize computing system 190 to send feedback to computing device 150. As one example, computing device 150 may receive data indicating a request to adjust a characteristic (e.g., size, positioning characteristics, orientation characteristics, etc.) of future dental appliances designed according to transform data output by the neural network for the general patient cohort of patient 102.

In some examples, computing system 150 updates practitioner preferences library 168 based on the received practitioner feedback (220). The optional nature of step 220 is illustrated in FIG. 2 by way of dashed-line borders. In some examples, neural network engine 184 may use data available from practitioner preferences library 168 (updated on an ongoing basis using incoming feedback from practitioners) to train the neural network on an ongoing basis.

Figure 3:
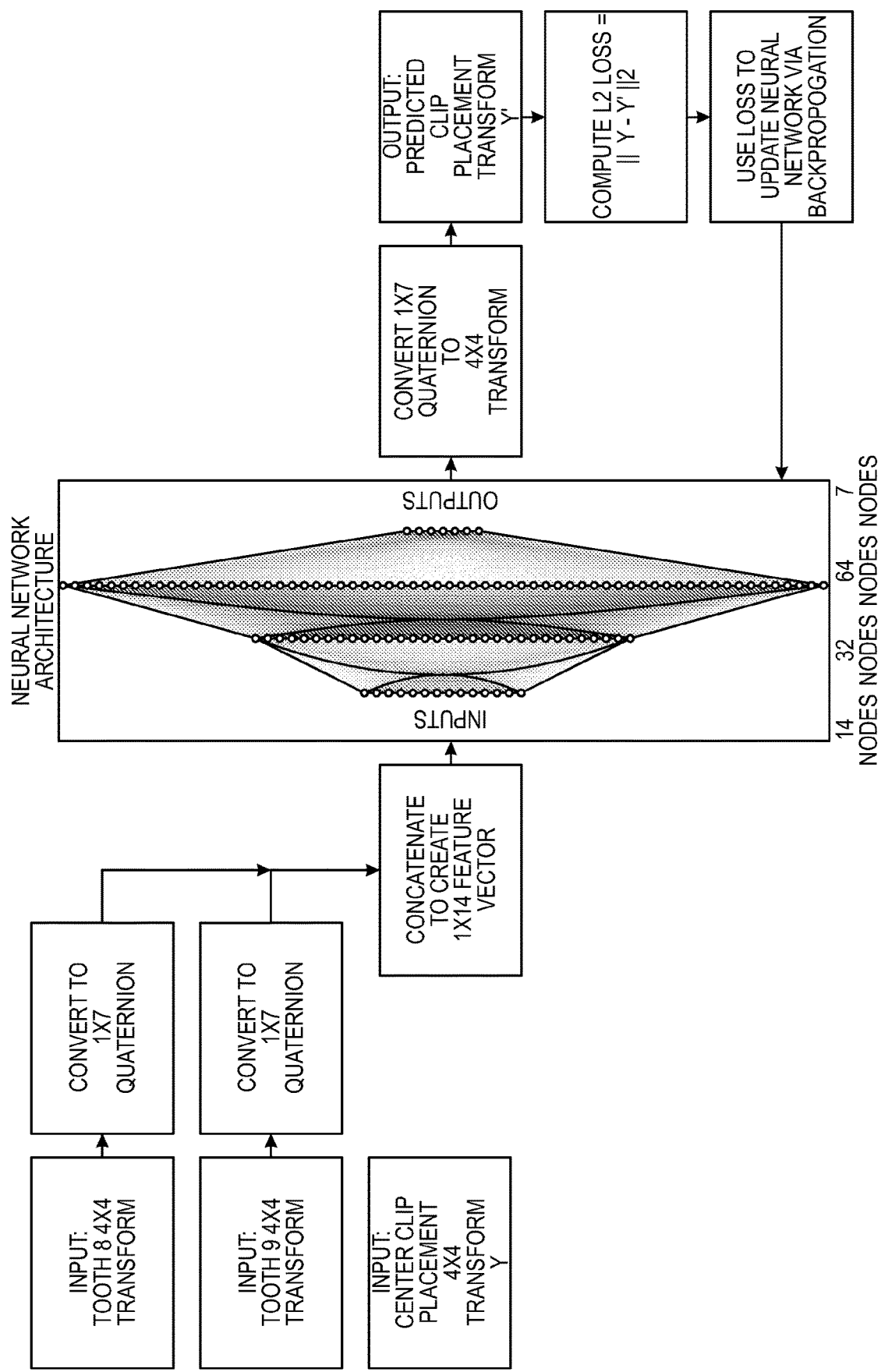
FIG. 3 is a flow diagram illustrating an example use of a neural network for placement of a library component of a dental appliance in accordance with aspects of this disclosure.

FIG. 3 is a flow diagram illustrating an example use of a neural network for placement of a library component of dental appliance 112, in accordance with aspects of this disclosure. FIG. 3 is described with respect to the example of using a two-hidden-layer neural network to determine placement of a center clip registration tab at a specified position and orientation relative to the two maxillary central incisors ("teeth 8 and 9" as denoted in the universal notation system for permanent teeth). The center clip's origin is to be placed at approximately the midpoint of the two maxillary central incisors, and to be oriented such that the center clip's vertical (or 'Y') axis is normal to the archform in which the maxillary incisors are positioned.

Neural network engine 184 may implement a backpropagation-based training of the neural network, using one 4×4 transform for each of the maxillary central incisors, and one 4×4 transform that defines the ground truth position and orientation of a post-placement center clip. Neural network engine 184 may extract the transforms for the maxillary central incisors from the 3D mesh data that describe the current dentition of patient 192. Neural network engine 184 may obtain the ground truth transform from various sources, such as manual production by a technician using a CAD tool to position and orient the center clip, or alternatively, via automatic generation, such as by using the techniques described in WO 2020/240351, filed May 20, 2020.

In the example of FIG. 3, neural network engine 184 converts each of the 4×4 transforms for the maxillary central incisors to a respective 1×7 quaternion vector. Neural network engine 184 concatenates these two 1×7 quaternion vectors to yield a single 1×14 feature vector. The 1×14 feature vector corresponds to a single patient's data (hereinafter, a single "case"). An 'n' by 14 matrix may be formed by laterally concatenating the feature vectors for 'n' cases, where 'n' denotes a nonnegative integer value.

In this way, neural network engine 184 may encode data for multiple cases into a single matrix that can be used as a training input to train the two-hidden-layer neural network of FIG. 3. Neural network engine 184 may use the backpropagation algorithm to train the neural network in some non-limiting examples of this disclosure. The layers of the neural network are fully connected, meaning that a weighted connection exists between a node i in a first layer, and each of the nodes j in the next layer.

The backpropagation training algorithm executed by neural network engine 184 adjusts these weights through the overall course of training (e.g., through multiple iterations or passes of training and fine tuning thereof) to gradually encode the desired logic into the neural network over the course of multiple training iterations/passes. According to the specific example illustrated in FIG. 3, neural network engine 184 uses a fully connected feedforward neural network with two hidden layers. With FIG. 3 being read from left to right, the first and second hidden layers have dimensions of 1×32 and 1×64 respectively, and the output dimensions are 1×7.

In other examples consistent with the techniques of this disclosure, neural network engine 184 may utilize other neural network architectures and techniques, such as a Recurrent Neural Network (RNN), restricted Boltzmann machine (RBM), Long Short-Term Memory (LSTM), Convolutional Neural Network (CNN) technology, and various others. In other examples, such as those in which neural network engine 184 uses 3D meshes as inputs, neural network engine 184 may use a Graph CNN to generate placement information for one or more library components, such as the center clip discussed above.

In other examples still, neural network engine 184 may use an image of the maxillary central incisors (e.g., an image produced from a render could be taken of the two teeth) as an input to a CNN or a fully connected neural network to produce the placement transform of the library component. Neural network engine 184 passes the 14 input nodes' values along the weighted connections to the first hidden layer of FIG. 3. Neural network engine 184 passes each node value in the first hidden layer (with weighting factors in applicable scenarios) to each of the corresponding nodes in the second hidden layer, and so on.

Once the inputs have finished propagating through the neural network, neural network 184 converts the resulting 1×7 vector (interpreted as a quaternion) to a 4×4 matrix, which represents the predicted clip placement matrix. Neural network 184 then computes the layer normalization for the second layer (the "L2 Norm") of the difference between the placement matrix and the ground truth transform that was input as a 4×4 transform. The resulting difference represents a "loss" value, which neural network engine 184 may feed back into the neural network to update the weights via backpropagation.

After multiple iterations of this backpropagation process, the neural network is trained to take, as inputs, two teeth transforms (i.e. describing the positions and orientations of two teeth) and output a transform that positions a library part (e.g. the center clip) in between those teeth, and oriented normally to the archform. The program flow for the training of this particular example is shown in FIG. 3. Although FIG. 3 is described primarily with respect to the example of using a two-hidden-layer neural network, neural network engine 184 may train and execute more complex computational models in other examples, such as those of deep learning (e.g. a generative adversarial network or "GAN") in accordance with aspects of this disclosure.

Figure 4:
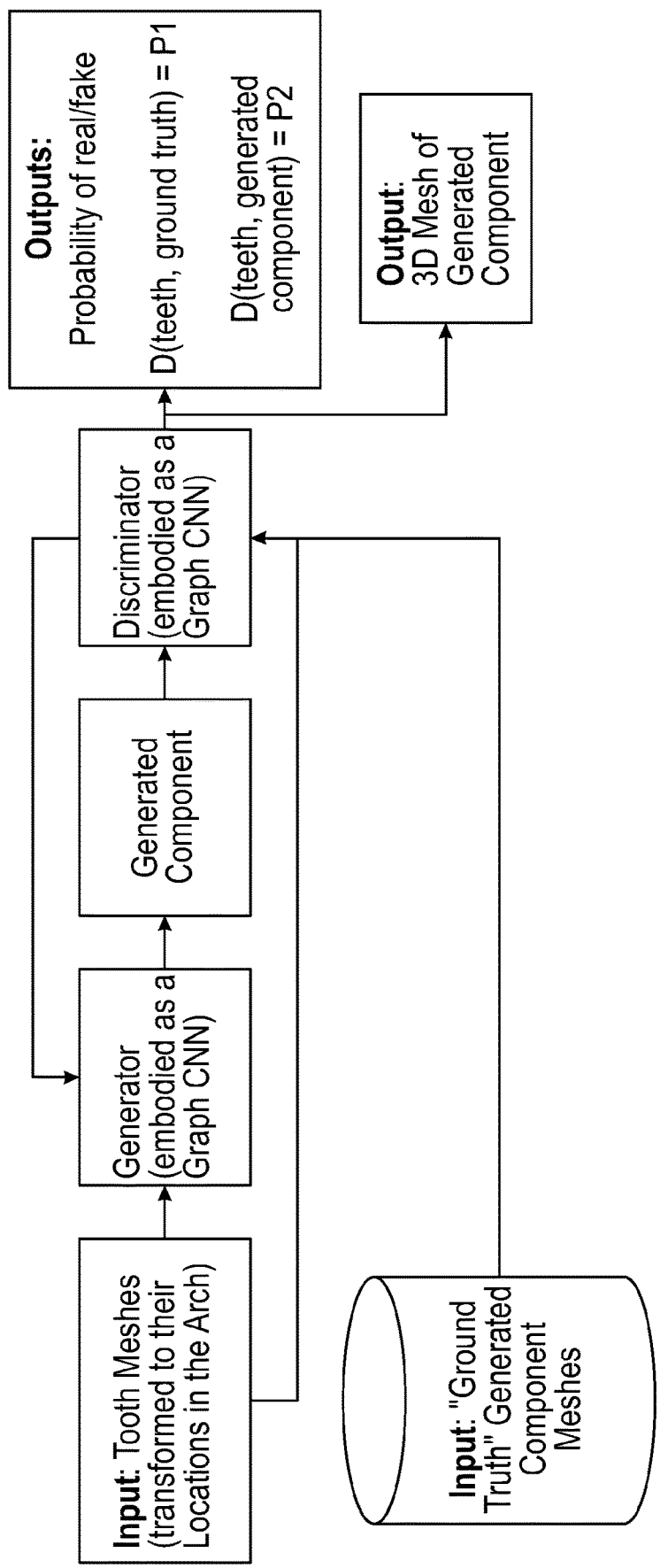
FIG. 4 is a flow diagram illustrating an example of neural network-based component geometry generation in accordance with aspects of this disclosure.

FIG. 4 is a flow diagram illustrating an example of neural network-based component geometry generation in accordance with aspects of this disclosure. Neural network engine 184 may train the neural network-based system of FIG. 4 to generate custom component(s), such as dental appliance 112 or discrete components thereof. In some examples, neural network engine 184 may generate a component, such as a mold parting surface using a Graph CNN. FIG. 4 is described herein with respect to implementing a CNN as the generator network component of a GAN.

In the examples described herein with respect to FIG. 4, the dentition of patient 102 (or of patients of prior cases) is described by a set of 3D meshes, with each tooth being represented by its own individual 3D mesh. If the transform of each tooth is suitably positioned and oriented to reflect that particular tooth's location in the archform, then each 3D mesh includes a list of vertices and a list of faces which describe the relationships between the vertices. In other words, each 3D mesh may specify which vertices are a part of which face.

In these examples, each face is a triangle. Neural network engine 184 inputs the 3D tooth meshes to the Graph CNN shown in FIG. 4. The Graph CNN, in turn, generates a component geometry as the output. The output represents the generated component in the form of another 3D mesh comprising respective vertices and faces. The Graph CNN may generate this 3D mesh in one of two pathways, namely 1) by generating a new set of vertices that describe the generated component; or 2) by moving a set of pre-existing vertices.

In the second technique (which involves moving a set of pre-existing vertices), the generator Graph CNN may start from a template or a generalized example of the generated component, and then manipulate the starting set of vertices to make the generated component conform to the dentition (e.g., current and/or intermediate in-treatment dental anatomy) of patient 102. In turn, neural network engine 184 feeds the pairing of the 3D mesh representing the component generated by the Graph CNN and the 3D tooth mesh originally input to the Graph CNN into a differentiable discriminator network.

Neural network engine 184 also feeds a second pairing into the differentiable discriminator network, namely, the pairing of the ground truth library component and the 3D tooth mesh originally input to the Graph CNN. The differentiable discriminator network computes the probability that the input pair came from the second dataset (i.e., the pairing that included the ground truth generated component). That is, the differentiable discriminator network computes the probability of each input dataset corresponds to a ground truth dataset including the original tooth meshes and the ground truth mesh of the target geometry.

The differential discriminator network produces gradients, which neural network engine 184 may use as a loss function for the generator network (in this case, implemented as a CNN) illustrated in FIG. 4. In the context of machine learning, a loss function quantifies the extent to which a machine learning model differs from an ideal model, and the loss function is used to guide the training of the machine learning model. The generator network may also use other loss functions, such as normalization of individual layers (e.g., the L1 Norm and/or the L2 norm) and the Chamfer distance (which is a sum of positive distances defined for unsigned distance functions). In other examples, neural network engine 184 may input an image of the maxillary central incisors (e.g., an image produced from a render taken of the two teeth) to a CNN or to a fully connected neural network to produce a mesh of the ground truth component.

In various examples, the ground truth generated components may be produced manually using a CAD tool, or automatically using the techniques described in WO 2020/240351, filed May 20, 2020. In some examples, subject to availability, neural network engine 184 may augment the training of the generator network using placement information for dental appliance 112, such as the transform output by the neural network of FIG. 2.

Although discussed primarily with respect to dental appliances (such as dental appliance 112) used in dental restorative treatment as an example, it will be appreciated that the neural network-based placement and/or geometry generation techniques of this disclosure can also be used with respect to other types of dental appliances. Non-limiting examples of other dental appliances that computing device 150 can customize using the techniques of this disclosure include a lingual bracket, an overall lingual bracket system, an orthodontic aligner (e.g., a transparent aligner or clear aligner), a bonding tray, etc. For instance, neural network engine 184 may train a GAN generator such as the Graph CNN generator of the GAN of FIG. 4, but using ground truth generated components used in these other types of dental appliances. In these examples, the trained generator Graph CNN may produce generated features for any of these other types of dental appliances, such as one or more mold parting surfaces. Examples of a geometry that neural network engine 184 may use to generate features of a lingual brackets are discussed below with reference to FIGS. 7 & 8.

For example, computing device 150 may invoke neural network 184 to generate placement and/or geometry information for a lingual bracket system that would otherwise be designed by technicians using custom software. As part of the design of the lingual bracket system, neural network engine 184 may generate specifications for a bonding pad for a specific tooth. Neural network engine 184 may train the neural network to subsume various steps of the custom software-based generation process, such as outlining a perimeter on the specific tooth, determining a thickness to form a shell, and subtracting out the specific tooth via a Boolean operation.

Neural network engine 184 may train the neural network to select bracket bodies from a library (e.g., appliance feature library or models library 166), virtually place the selected bracket body on the pad, and unite the pad and the bracket body mounted on it via Boolean addition operations. The neural network may adjust one or more bracket components (e.g. hooks, wings, etc.) to adapt the overall bracket to the particular geometry of the specific tooth and the adjacent gingiva. The neural network, when executed by neural network engine 184, may generate a design according to which the adjusted bracket component is united with the bracket body to complete the digital design of the overall bracket, and may export the overall bracket geometry.

Neural network engine 184 may encode the overall bracket geometry in various ways for export, such as in the form of a stereolithography (STL) file that stores 3D geometry information. To train the neural network for lingual bracket generation, neural network engine 184 may leverage past cases for a patient cohort. With a number of past cases being available for a variety of patients, neural engine 184 may train the neural network to implement automated design of lingual brackets with relatively little (or no) retraining, thereby conserving compute resource overhead, and with improved accuracy for specific dental anatomy idiosyncrasies of patient 102, thereby providing improved data precision.

Examples of custom appliance features that the generator network of the GAN may generate include 3D mesh-represented information for a spline, a mold parting surface, a gingival trim surface, a shell, a facial ribbon, a lingual shelf, a door, a window, among others. In one example, the generator network may generate one or more digital meshes representing splines for each slice of the dental anatomy. The generator network of the GAN may generate a spline for a given slice based on a plurality of tooth midpoints of teeth within the slice and/or closest points between adjacent teeth within the slice (e.g., points of contact between adjacent teeth within the slice or points of closest proximity between adjacent teeth within the slice). In other words, in this example, the generator network accumulates a set of points (e.g., tooth midpoints, points of contact between adjacent teeth, points of closest approach between adjacent teeth, or a combination thereof) for each slice to generate features representing a spline for each digital slice.

In some examples, the generator network generates a mold parting surface as one example feature to be incorporated within an overall 3D model of a dental restoration appliance. Neural network engine 184 may execute the generator network to generate the mold parting surface based on the plurality of midpoints and/or closest points between adjacent teeth. For example, the generator network may accumulate a plurality of the points for each spline for each slice to generate the mold parting surface. As one example, in an example where the generator network divides the dental anatomy into four slices and generates a single spline for each slice, the points of each of the four splines may be aggregated to generate the mold parting surface.

In one scenario, neural network engine 184 may feed preference information for dental practitioner 106 from practitioner preferences library 168 into the ground truth repository, to be used as training data augmentation. For instance, neural network engine 184 may query practitioner preferences library 168 to determine preferences for dental practitioner 106. Examples of data stored within practitioner preferences library 168 include a preferred size, positioning, or orientation of a pre-defined appliance feature for dental practitioner 106.

Neural network engine 184 may also train the generator network using data indicative of pre-defined appliance features, such as by accessing and retrieving the data from one or more libraries (e.g., as stored in a datastore, database, data lake, file share, cloud repository or other electronic repository) of 3D meshes representing pre-defined features for incorporation within an overall 3D model of dental appliance 112. For example, neural network engine 184 may receive these data by querying appliance feature library 164. Appliance feature library 164 stores data defining 3D meshes for a plurality of pre-defined appliance features, such as vents, rear snap clamps, door hinges, door snaps, an incisal registration feature (also referred to as a "beak"), among others.

In one example, neural network engine 184 selects one or more pre-defined appliance features of a plurality of pre-defined appliance features stored within appliance feature library 164. For example, appliance feature library 186 may include data defining a plurality of different predefined appliance features of a given type of pre-defined appliance feature. As one example, appliance feature library 164 may include data defining different characteristics (e.g., size, shape, scale, orientation) for a given type of pre-defined appliance feature (e.g., data for differently sized and/or differently shaped hinges, etc.). In other words, appliance feature library 164 may determine the characteristics of a pre-defined appliance feature and select a feature from the pre-defined appliance library that corresponds to the determined characteristics.

In some scenarios, neural network engine 184 selects, for training data augmentation, a pre-defined appliance feature (e.g., a particularly sized door hinge) from appliance feature library 164 based on landmarks for a corresponding tooth, characteristics (e.g., size, type, location) of the corresponding tooth (e.g., a tooth for which the appliance feature will be used to restore when the dental appliance is applied to the patient), practitioner preferences, or both.

In other examples, appliance feature library 164 includes data defining a set of required pre-defined appliance features. In some such examples, neural network engine 184 may retrieve data for the 3D meshes representing the pre-defined features for each of the required pre-defined features to use as additional training data. In such examples, the generator network of the GAN may transform the 3D mesh for including in the patient specific dental appliance. For example, the generator network may rotate or scale (e.g., re-size) a 3D mesh for a particular feature based on the landmarks for a corresponding tooth, characteristics of the tooth, and/or practitioner preferences.

Figure 5:
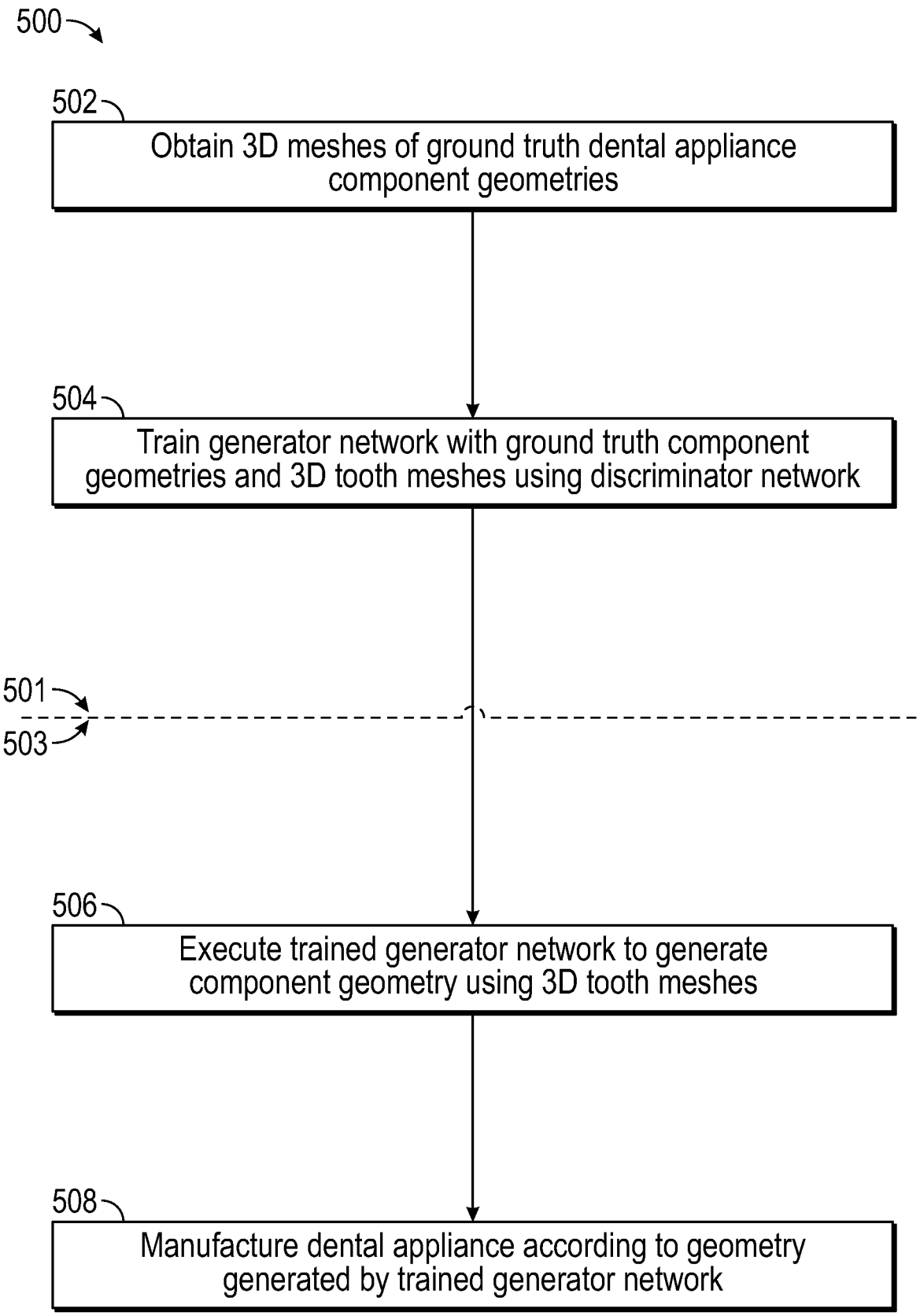
FIG. 5 is a flowchart illustrating a process that a computing device may implement to generate component geometries using a GAN, according to aspects of this disclosure.

FIG. 5 is a flowchart illustrating process 500 that computing device 150 may implement to generate component geometries using a GAN, according to aspects of this disclosure. Process 500 generally corresponds to techniques described above with respect to FIG. 4. Process 500 may begin with training phase 501, in which neural network engine 184 obtains 3D meshes of ground truth dental appliance component geometries (502). In various examples, neural network engine 184 may obtain the 3D meshes of the ground truth dental appliance component geometries from sources that provide manually generated component geometries, or sources that provide component geometries automatically generated using the techniques described in WO 2020/240351, filed May 20, 2020.

Also as part of training phase 501, neural network engine 184 may train a generator network (e.g., the Graph CNN of FIG. 4) with the ground truth component geometries and 3D tooth meshes using a discriminator network (504). For example, neural network engine 184 may train the generator network by feeding {generated component geometry, 3D tooth mesh} pairs and {ground truth component geometry, 3D tooth mesh} pairs into the discriminator network. Neural network engine 184 may execute the discriminator network to calculate probabilities for each pairing, indicating whether or not the respective pairing is based on a ground truth component geometry.

While step 504 is illustrated in FIG. 5 as a single step purely for ease of illustration, it will be appreciated that neural network engine 184 runs the discriminator network in multiple iterations to train the generator network and continually fine-tune the training until the generator network generates component geometries that are sufficiently accurate to "spoof" ground truth geometry-based pairings with respect to the discriminator network.

Once neural network engine 184 determines that the generator network is sufficiently trained, neural network engine 184 may temporarily shelve or potentially even permanently discard the discriminator network for execution phase 503 of process 500. To begin execution phase 503, neural network engine 184 may execute the trained generator network to generate a component geometry using 3D tooth meshes of the current dental anatomy of patient 102 as inputs (506).

In one non-limiting example, neural network engine 184 may execute the trained generator network to generate a mold parting surface of dental appliance 112 by executing the trained generator network. In turn, manufacturing system 194 manufactures dental appliance 112 according to the component geometry generated by the trained generator network (508). For example, computing device 150 may output a 3D mesh of the component geometry generated by neural network engine 184 to computing device 192 of manufacturing facility 110 by invoking network interface hardware of communication unit(s) 176 to transmit packetized data over network 114.

FIG. 6 is a rendering illustrating an example center clip placement performed according to the neural network-based placement techniques of this disclosure discussed above with respect to FIGS. 2 and 3. In the two views illustrated in FIG. 6, the center clip is placed between (e.g., centered at or substantially at the midpoint of) the two maxillary central incisors (teeth 8 and 9 according to the universal numbering system for permanent teeth) and oriented to be normal to the archform in the proposed dental anatomy of patient 102.

Figure 7:
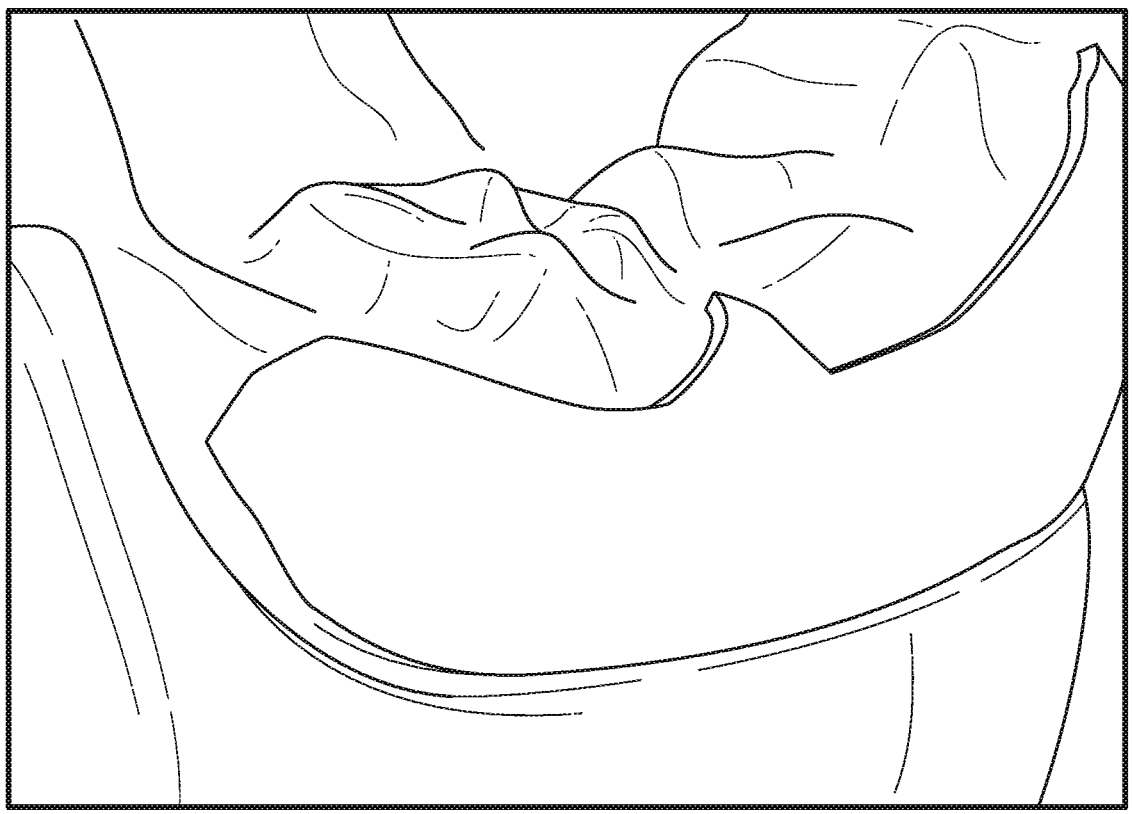
FIG. 7 is a rendering illustrating an example of a bonding pad (e.g., of a lingual bracket) that is customized to the shape of the corresponding tooth.

FIG. 7 is a rendering illustrating an example of a bonding pad (e.g., of a lingual bracket) that is customized to the shape of the corresponding tooth. As described above, the GAN-based techniques described with respect to FIGS. 4 & 5 may be used to generate the geometry of such bonding pads.

Figure 8:
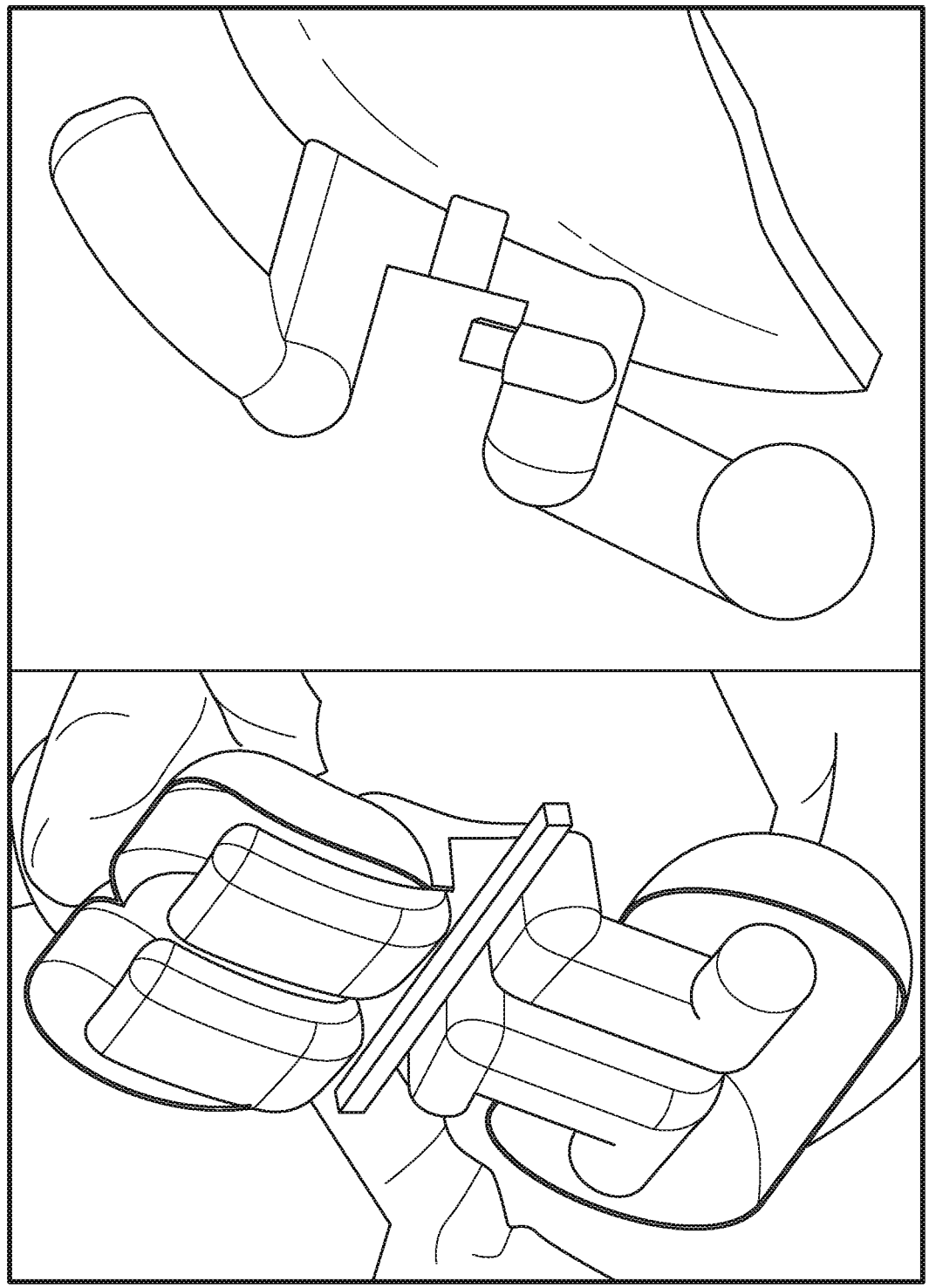
FIG. 8 is a rendering illustrating an example of a set of components that make up a lingual bracket.

FIG. 8 is a rendering illustrating an example of a set of components that make up a lingual bracket. The techniques described above with respect to FIGS. 1-5 may be used to assemble brackets such as the overall bracket shown in FIG. 8, and/or to generate placement information for the bracket on the teeth of patient 102.

Figure 9:
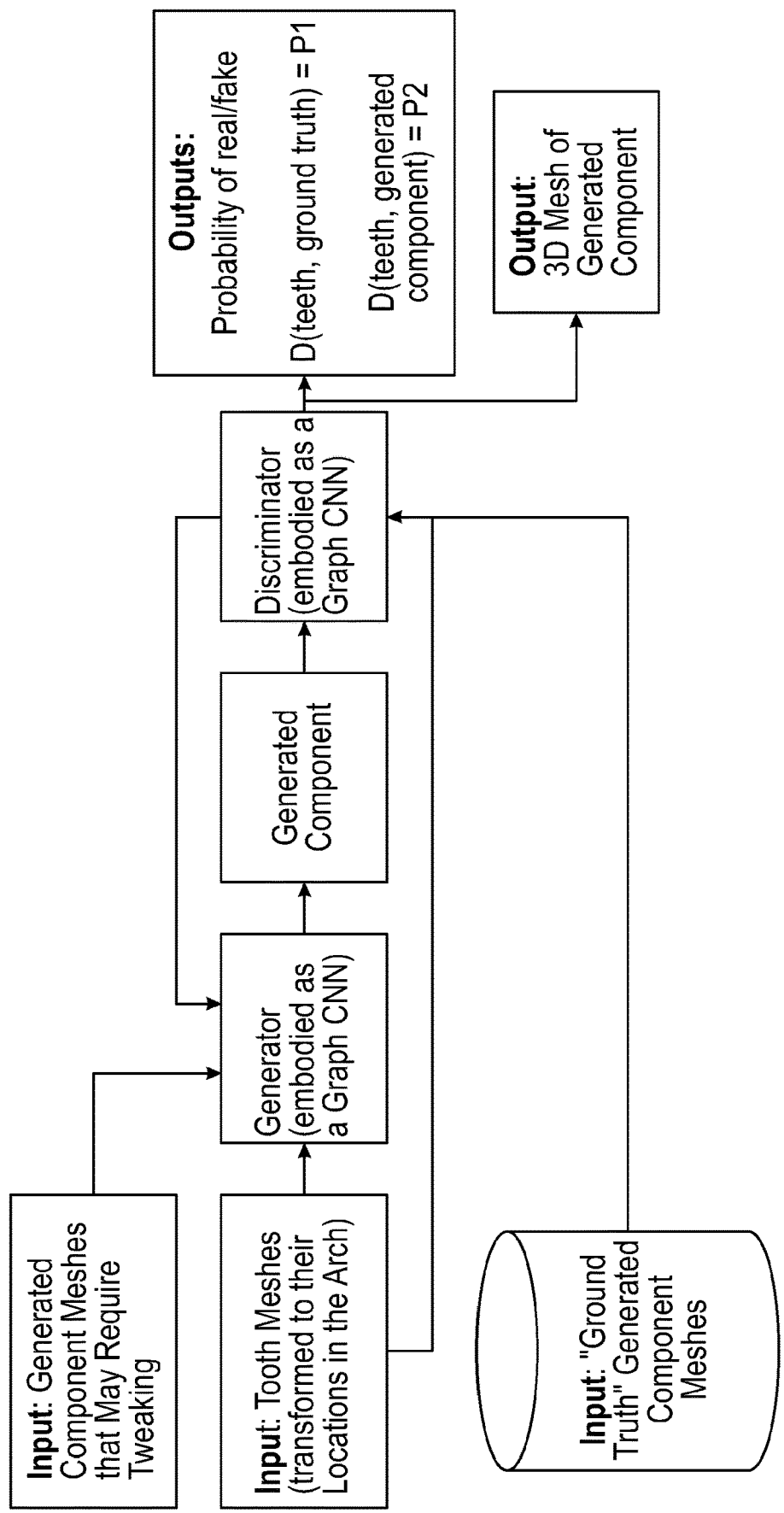
FIG. 9 is a a flow diagram illustrating another example of neural network-based component geometry generation in accordance with aspects of this disclosure.

FIG. 9 is a flow diagram illustrating another example of neural network-based component geometry generation in accordance with aspects of this disclosure. Neural network engine 184 may train and execute the generator network of the GAN shown in FIG. 9 to refine or fine-tune a previously generated dental appliance model to form an updated dental appliance model or updated model of a component thereof. Neural network engine 184 may refine (or fine-tune or "tweak") the geometry of dental appliance models that are automatically generated using landmark information (e.g., using the techniques described in WO 2020/240351, filed May 20, 2020) or the geometry of dental appliance models generated manually using a computer-aided design (CAD) tool to form the updated model (e.g., updated 3D) of this disclosure.

The GAN generator-based refinement of a previously generated model provides a time reduction, and in many instances, an improvement in accuracy and data precision with respect to geometry modifications required to render the dental appliance model viable (the updated model representing the viable dental appliance component for use in dental restoration treatment). Upon being trained to sufficiently spoof the discriminator network and/or to pass visual inspection, the generator network is configured to gradually modify component design to bring the updated model of the dental appliance geometry in line with a design that is usable during dental restoration treatment of patient 102.

In contrast to the techniques described with respect to FIG. 4 (in which a component geometry is designed entirely by the generator network of the GAN), the techniques associated with FIG. 9 combine the computational result from landmark-based automation tools (e.g., the automation tools described in WO 2020/240351, filed May 20, 2020) or a manually generated geometry with neural network-based fine-tuning to finalize the design with any last-mile tweaks (to form the updated component model) that may be beneficial to the dental restoration treatment of patient 102. The GAN of FIG. 9 provides fast convergence times, enabling computing device 150 to provide the benefits of both the initial geometry design using landmark-based techniques and neural network-based geometry refinements in computationally fast manner to generate the updated component model.

The GAN of FIG. 9 enables generator network training even in cases of having limited numbers of previously generated models to use as examples for training. In this way, the GAN of FIG. 9 leverages engineered factors of the originally designed geometry in cases in which training data are limited, while implementing the benefits of neural network-based design for last-mile tweaking of the original design. In comparison to the GAN of FIG. 4, the GAN of FIG. 9 provides the generator network an additional input (in both the training phase and the execution phase) with an original appliance geometry that may need tweaking to bring it to final form (in the form of the updated model or updated component 3D mesh) for fabrication (e.g., via 3D printing) by manufacturing system 194.

Figure 10:
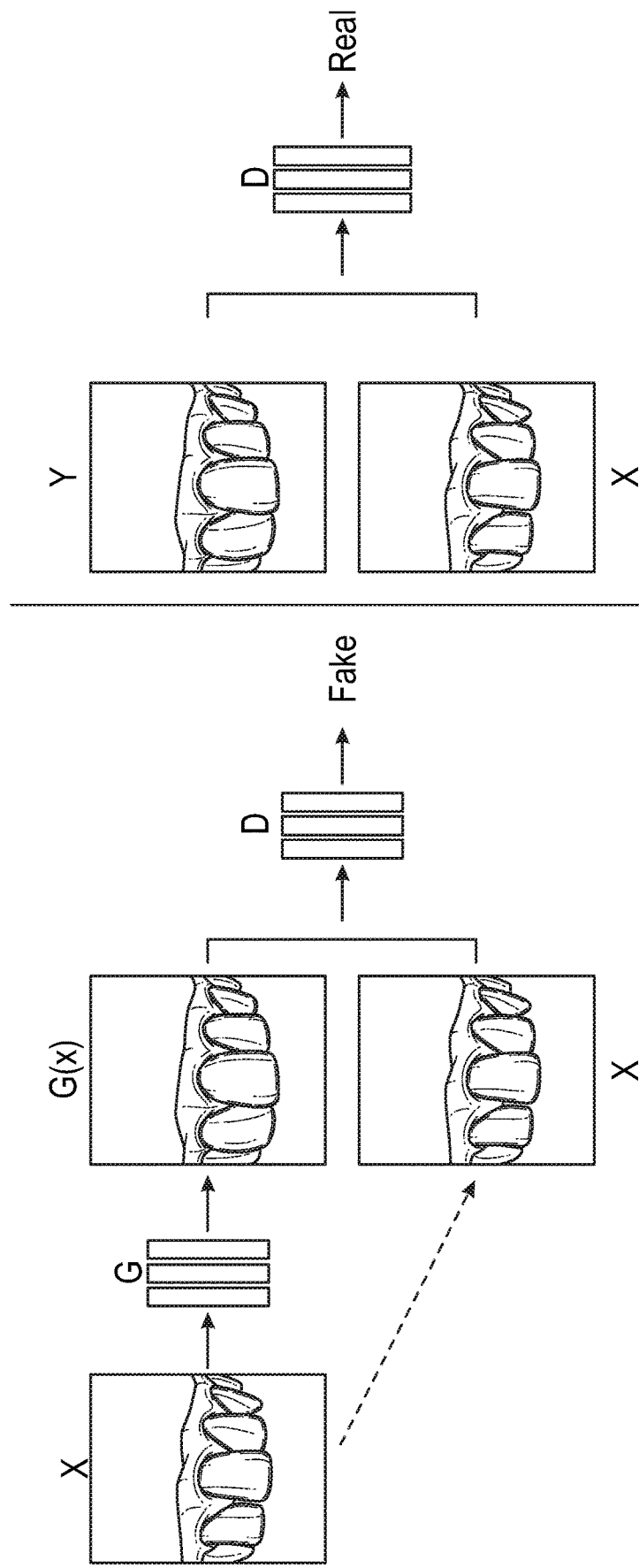
FIG. 10 is a conceptual diagram illustrating the symbiotic training processes for the generator network and discriminator network of a cGAN configured to render 2D images of a proposed dental anatomy for a patient according to aspects of this disclosure.
Figure 11B:
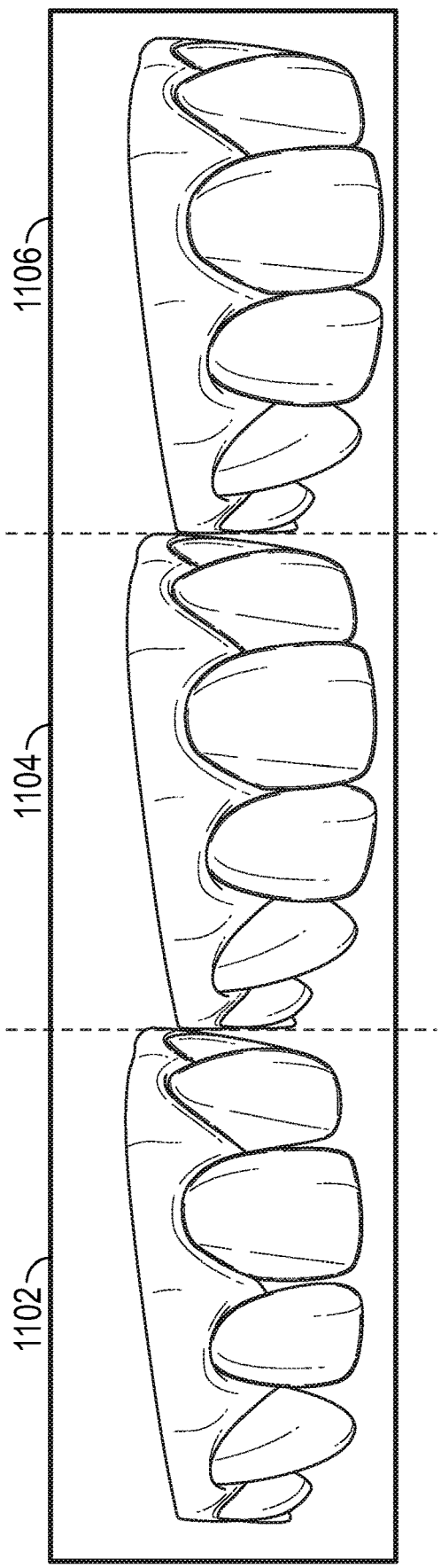
FIG. 11B illustrates a comparison between a current dental anatomy image, a proposed dental anatomy image of this disclosure, and a ground truth restoration image.
Figure 12:
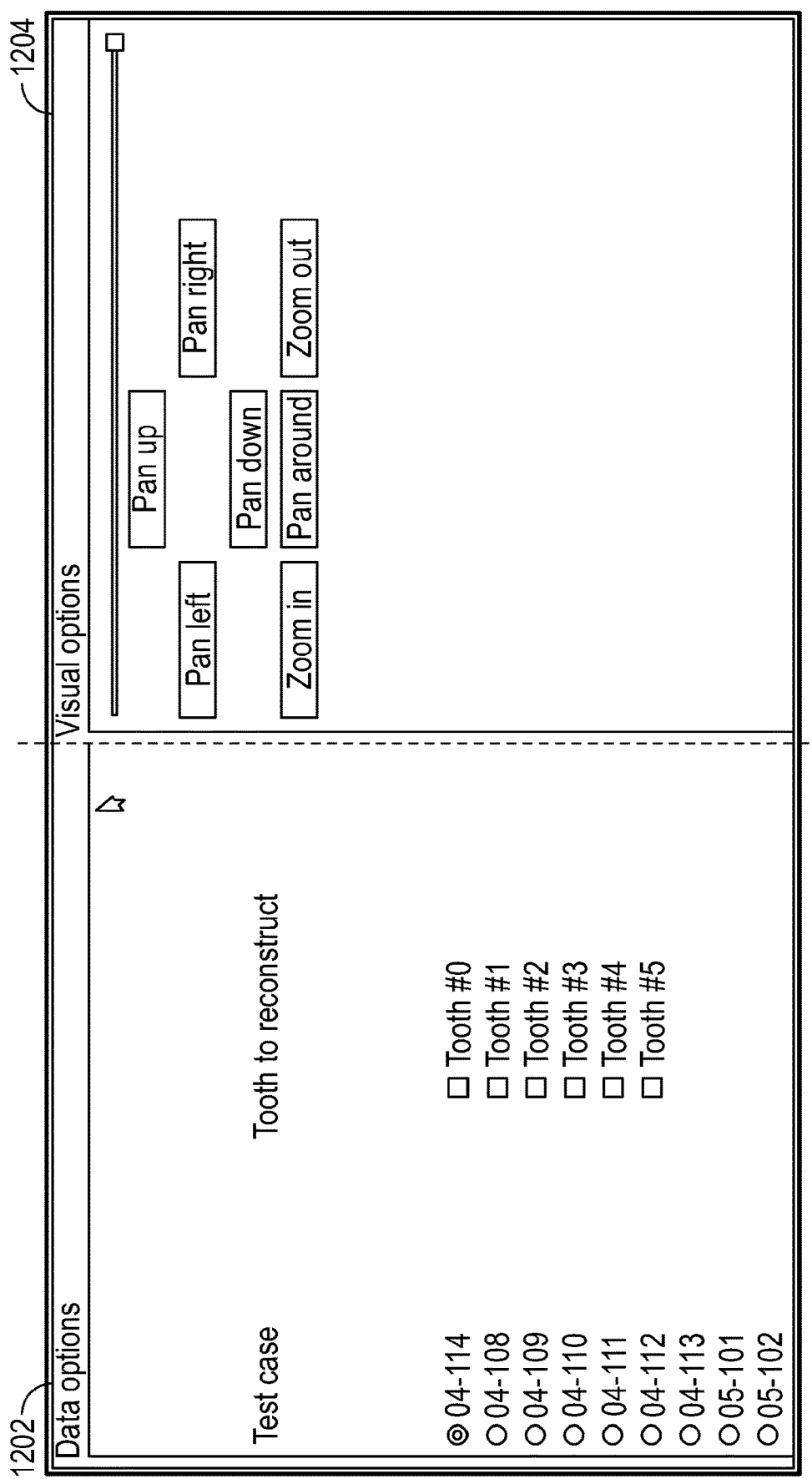
FIG. 12 illustrates menus that a computing device of FIG. 1 may display as part of a graphical user interface (GUI) that includes a current dental anatomy image and/or a proposed dental anatomy image of this disclosure.

FIGS. 10-12 are directed to aspects of this disclosure that describe systems configured to display proposed dental restorations to patient 102 via an automated design process using generative modeling. According to these aspects of this disclosure, neural network engine 184 utilizes data collected from dental practitioner 106 and/or other trained clinicians/technicians to train a neural network configured to generatively model the proposed dental anatomy of patient 102. For instance, neural network engine 184 may train the neural network to learn attributes of an acceptable dental restoration in a data-driven manner. Examples of this disclosure are described with respect to generating a unique two-dimensional (2D) image of a post-restoration proposed dental anatomy for a single patient (patient 102 in these examples).

The neural network-based generative display techniques of this disclosure are described below with respect to dental restoration, by way of the non-limiting example of 2D image generation for a (post-restorative) proposed dental anatomy. However, it will be understood that the neural network-based generative display techniques of this disclosure can also be applied with respect to other areas, such as to assist in 3D printing of ceramic and/or composite dental crowns, etc. The goal of various dental restorative treatments discussed herein is to provide patient 102 with a composite restoration for damaged or unaesthetic teeth at a low cost with minimal invasiveness, or to provide dental restoration for other sub-optimal conditions associated with the current dental anatomy of patient 102.

Patient 102 (or any other patient) interested in dental restoration may have his/her current dental anatomy scanned at clinic 104. The neural network-based generative modeling techniques of this disclosure provide a process-fast and data-precise 2D image view of the post-restoration proposed dental anatomy, custom-tailored for a given patient (patient 102 in this particular example). The neural network-based generative modeling techniques of this disclosure mitigate significant lead time and costs from existing solutions for dental restoration planning.

To improve data precision with respect to generative modeling of post-restoration 2D imaging of the proposed dental anatomy of patient 102, neural network engine 184 may incorporate dental restoration styles (e.g., youth, geriatric, natural, oval, etc.) into the training data if style information is available for past cases. In these and/or other examples, neural network engine 184 may incorporate one or more of accepted "golden proportion" guidelines for the size of teeth, accepted "ideal" tooth shapes, patient preferences, practitioner preferences, etc. into the training data used to train the neural network. If different styles are available in the training dataset, then patient 102 may have the ability to view different restoration options generated by the algorithm in different styles. In other words, neural network engine 184 may generate different style options with respect to the proposed post-restorative dental anatomy of patient 102 based on differently styled outcomes in past cases.

By training the neural network with these dental restoration-related training data (usually over numerous training iterations for fine-tuning), neural network engine 184 improves data precision with respect to generatively modeling the proposed dental anatomy of patient 102, reduces the computational resource expenditure at runtime (by executing a precisely trained neural network), and reduces the overall process time for generating the dental restoration treatment plan, by reducing the iterations needed to correct or fine-tune multiple attempts at planning a treatment for a given patient for a single round of dental restorative treatment.

Computing devices 150 and 190 provide various user experience-related improvements as well, by way of computing device 150 implementing the neural network-based generative modeling techniques of this disclosure. For example, dental practitioner 106 may present patient 102 with 2D image of the proposed post-restoration dental anatomy by generating the 2D image relatively quickly (and potentially during the same patient encounter) upon scanning the current dental anatomy of patient 102. In some examples, dental practitioner 106 may synthesize different post-restorative outcomes (e.g., using different styles or other preference-related factors) to enable patient 102 to view different options to aid in choosing a dental restoration plan.

In some examples, dental practitioner 106 may provide a "pre-approved" target for the generation of a 3D restoration file, which can be used in the design and/or manufacture processes of dental appliance 112. Providing pre-approved plan information (which neural network engine 184 may obtain from practitioner preferences library 168 or other sources) enables neural network engine 184 to train the neural network to generate custom-tailored dental restoration models with reduced amounts of practitioner input, compressing the production process for custom products.

Because patient 102 can visualize a potential post-restoration outcome of his/her own dental anatomy rather than past cases of other patients, neural network engine 184 leverages training data to provide individualization as a user experience improvement in these examples, as well. The generative modeling techniques of this disclosure may be applicable to areas other than dental restoration in which a patient is interested in a unique or customized solution as well, such as with respect to respirators, bandaging, etc.

According to some examples of this disclosure, neural network engine 184 uses a GAN to generate the 2D image of the proposed dental anatomy of patient 102 for the post-restorative treatment stage. As described above, GANs utilize a pairing of differentiable functions, often deep neural networks, with the goal of learning the generation of an unknown data distribution. The first network, known as the generator network, produces a data sample given some input (e.g., random noise, conditional class label, etc.). The second network, known as the discriminator network, attempts to classify the data generated by the generator from a real data point coming from the true data distribution.

As part of the training, the generator network continuously tries to spoof (or "fool" or "trick") the discriminator into classifying data generated de novo as "real." As the success rate of spoofing the discriminator network using the generated data becomes more frequent, the training outputs of the generator network become more realistic. In some examples of the generative 2D modeling techniques of this disclosure, neural network engine 184 uses a conditional GAN (cGAN), where the generator network is conditioned on a 2D rendered image of a 2D scan of the current dental anatomy of patient 102.

The generator network, which is a CNN in some non-limiting examples, takes as input a rendered 2D image of the current (pre-restoration) dental anatomy of patient 102, and generates a 2D image of how the proposed (post-restoration) dental anatomy of patient 102 would appear, based on the current state of the adversarial training of the generator network. The generator network may also accept as input data (depending on availability and/or relevance) additional information such as which teeth are to be restored, the restoration style (e.g. youth, geriatric natural, oval, etc.), etc.

The discriminator network, which may also be a CNN in some examples, receives a pair of 2D images as input. The first pair contains a rendered 2D image of the pre-restoration dental anatomy of a patient and a rendered 2D image of the true restoration performed by a clinician (which is classified as a "real" or "ground truth" pairing) for the same patient.

The second pair of images contains a rendered 2D image of before restoration and a generator network-generated restoration. The generator and discriminator networks are trained simultaneously, in an alternating fashion, improving upon each other to reach a shared goal of a precisely trained generator network.

In some embodiments, neural network engine 184 implements the generator network of the 2D restoration image aspects of this disclosure as an encoder-decoder CNN. In these examples, the generator network reduces the dimensionality of the input image, and then expands the dimensionality back up to the original dimensionality (e.g., via a sequence of downsampling and upsampling, or in other ways). The generator network in these examples may also be referred to as a "U-Net." As used herein, a "U-Net" refers to a type of encoder-decoder architecture in which the feature maps from the encoder are concatenated onto the respective feature maps in the decoder.

In a traditional GAN, the discriminator network receives either a real image (coming from the input dataset of images) or a syhtnesized image (which was produced by the generator). The output of the discriminator network is a probability in the range [0,1] representing the probability of the input image being a real image (coming from the dataset). In some implementations of the 2D restoration image aspects of this disclosure, the discriminator network is a "patch-GAN" discriminator network.

While a typical discriminator network outputs a single value representing the perceived realness of the input, a patchGAN discriminator network outputs an [n×n] matrix, where each element represents the perceived realness of a corresponding patch of the input. The perceived realness as represented by each element of the [n×n] output matrix represents the probability of the corresponding patch of the input image being part of a real or ground truth image. The discriminator network is implemented internally as a CNN.

FIG. 10 is a conceptual diagram illustrating the symbiotic training processes for the generator network and discriminator network of a cGAN configured to render 2D images of a proposed dental anatomy for patient 102 according to aspects of this disclosure. Aspects of FIG. 10 also illustrate the manner in which various data are handled by the generator and discriminator networks. In FIG. 10, "G" denotes the generator network of the cGAN, and "D" denotes the discriminator network of the cGAN. The pre-restoration 2D image (which is the input to G and half of the image pairing supplied by G to D) is denoted by "x". "G(x)" denotes the 2D image of the proposed restoration generated by G, given x as the pre-restoration input. The 2D rendered image of the actually performed dental restoration (or "true" or "ground truth" image of the post-restoration dental anatomy) is denoted by "y."

The particular use case scenario illustrated in FIG. 10 is associated with an unsuccessful iteration during the multi-iteration training process of G. As shown in FIG. 10, D outputs a decision that the combination of G(x) with x is a "fake." In contrast, and as intended with respect to adversarial cGAN training, D outputs a decision of "true" upon evaluating an input combination of x and y. In some examples, if D is a sufficiently trained and refined network, then after G is adversarially trained more precisely over future iterations of cGAN training, G may generate instances of G(x) that, when fed into D with x, successfully spoof D into outputting "true" decisions.

In these examples, upon G reaching this level of training, neural network 184 may begin executing G to generate, from an input of x, proposed 2D images of post-restoration dental anatomies of patient 102. In some examples, because G and D are trained in tandem, both networks may be untrained for similar periods of time. In these cases, both G and D may undergo training until G passes qualitative inspection, such as by passing a visual inspection by dental practitioner 106 or another clinician. Following the formats used above, 'x' represents the 2D pre-restoration image, 'y' is the ground truth 2D restored image, and G(x) is the image generated by the G given the pre-restoration image input. The total loss term used in some examples is a combination of L1 loss and GAN loss, given by equation (1) below:

$$\text{total}_{error_G} = gan_{loss_g} + (\lambda_{L1} * L1_{loss}) \tag{1}$$

The L1 loss is the absolute value of the difference between y and G(x), with the total loss being applied to G, but not to D. The calculation of the L1 loss is given by equation (2) below, where $\lambda_{L1}$ is 10 in this particular example, although it will be appreciated that $\lambda_{L1}$ can have other values in other examples consistent with this disclosure.

$$L1_{loss} = \lambda_{L1} * abs(y - G(x))$$

By leveraging the communicative connection to computing device 150 over network 114, computing device 190 may provide a chair-side application that enables dental practitioner 106 to show patient 106 a 2D rendering of one or more proposed restoration plans, often during the same patient visit during which the scan of the current dental anatomy is taken (and sometimes, very shortly or immediately after the scan is taken). Rather than displaying past cases of other patients or a general model which covers hypothetical patients, computing device 190 may use a cGAN executed by neural network engine 184 to output a custom rendering of the proposed dental anatomy for one or more post-restoration scenarios applicable specifically to the current dental anatomy and treatment plan(s) for patient 102.

That is, neural network engine 184 may implement generative modeling techniques of this disclosure in such a way that dental practitioner 106 can leverage cloud computing interactions to render a 2D image of proposed dental anatomies for one or more dental restoration plans applicable specifically to the current dental anatomy of patient 102. From the perspective of those at clinic 104, given a scan of the current dental anatomy of patient 102, computing device 190 quickly (or almost immediately) processes the scan and leverages cloud computing capabilities to render 2D images of one or more post-treatment dental anatomy images specific to the dentition of and treatment options available to patient 102.

In this way, neural network engine 184 may implement the generative modeling techniques of this disclosure entirely in the image domain, without requiring the potentially time-consuming generation of a 3D mesh. Upon approval (e.g., by patient 102 and/or by dental practitioner 106), computing device 190 may communicate the generated 2D image via network 114 to computing device 192, enabling manufacturing system 194 to generate a 3D mesh of dental appliance 112, or to directly manufacture dental appliance 112.

In some examples, neural network engine 184 may generate or regenerate the 2D image of the proposed dental restoration to incorporate patient-specified modifications, such as a restoration style selection or other parameters. In one such example, neural network engine 184 may implement a feedback loop within the cGAN to accommodate patient-provided or practitioner-provided modifications with respect to restoration style, tooth shaping, etc.

In one example, the trained generator network of the cGAN may enable a technician to create a 3D mesh from the 2D image output by the trained generator network. In another example, the 3D mesh can be automatically generated from the 2D image of the proposed dental anatomy output by the trained generator network. In one or more of these examples, the 3D mesh may be used as an input to the systems described above with respect to FIGS. 3 & 4. In some examples, dental practitioner 106 or other clinician at clinic 104 may use image capture hardware (e.g., a still camera or video camera) to obtain a photograph of the current dental anatomy of patient 102. In these examples, computing device 190 may generate a rendering of the current dental anatomy of patient 102 using the captured photograph.

As such, according to various examples of this disclosure, computing devices 190 and 150 may obtain a 2D image (whether a dental scan or a photograph) of a 3D object (in this case, the dentition of patient 102), and use the 2D image to generate another 2D image of the proposed dental anatomy (or a portion thereof) with respect to the proposed dental restoration treatment of patient 102. In this way, computing devices 190 and 150 may enable dental restoration modeling in a computationally light and process-fast manner, while maintaining data precision with respect to the dental restoration modeling, using the neural network training mechanisms of this disclosure.

In some examples, neural network engine 184 may execute the trained version of generator network G as an input generation system with respect to the neural networks illustrated in FIGS. 3 & 4. For instance, neural network engine 184 may augment the transform matrix inputs to the neural network of FIG. 3 and/or the tooth mesh inputs to the generator network of FIG. 4 with a 2D image of the proposed dental anatomy of patient 102. In these instances, neural network engine 184 avails of the output of the trained version of generator network G to train the neural network of FIG. 3 and/or the generator Graph CNN of FIG. 4 in a more holistic way, accounting for effects on a greater proportion of the archform of the dentition of patient 102 for which placement and/or geometry information are being generated.

FIG. 11A illustrates the input and output of a cGAN-trained generator network configured to generate a 2D image of a proposed dental anatomy using a 2D rendering of a current dental anatomy of patient 102. Current dental anatomy image 1102 illustrates the 2D rendering of the current dental anatomy of patient 102. Upon being cGAN trained (e.g., by successfully fooling the discriminator network at least a threshold number of times), the generator network ('G') of FIG. 10 uses current dental anatomy image 1102 to generate proposed dental anatomy image 1104.

Current dental anatomy image 1102 is a 2D rendering of the pre-restoration dentition of patient 102. Proposed dental anatomy image 1104 is a 2D rendering of a projection of the end result of one proposed dental restoration treatment plan for patient 102. As such, FIG. 11 shows a working example of one use case scenario in which a cGAN-trained iteration of generator network G performing the generative modeling techniques of this disclosure.

FIG. 11B illustrates a comparison between current dental anatomy image 1102, proposed dental anatomy image 1104, and a ground truth restoration image 1106.

FIG. 12 illustrates menus that computing device 190 may display as part of a graphical user interface (GUI) that includes current dental anatomy image 1102 and/or proposed dental anatomy image 1104. Data menu 1202 presents dental practitioner 106 or another clinician with various options to manipulate the content of the generative modeling. In the example of FIG. 12, data menu 1202 presents options of selectable test cases upon which to build the dental restoration plan. Data menu 1202 also includes tooth options, which enable dental practitioner 106 to select particular teeth from current dental anatomy image 1102 for which reconstruction is to be modeled.

Visual option menu 1204 enables dental practitioner 106 to adjust various viewing parameters with respect to the display of current dental anatomy image 1102 and/or proposed dental anatomy image 1104. Dental practitioner 106 may adjust various viewing parameters via visual option menu 1204 to enable patient 102 to better see the details of proposed dental anatomy image 1204.

In this way, dental practitioner 106 or other clinicians may operate computing device 190 at clinic 104 to effectuate cloud interactions over network 114, thereby leveraging the neural network-based generative modeling functionalities provided by computing device 150. By operating data menu 1202, dental practitioner 106 may provide the restoration modeling parameters that neural network engine 184 uses in generating proposed dental anatomy image 1204. By operating visual option menu 1204, dental practitioner 106 uses computing device 190 as an onsite display that customizes the viewing parameters of proposed dental anatomy image 1204 to suit the viewing needs and preferences of patient 102.

Figure 13A:
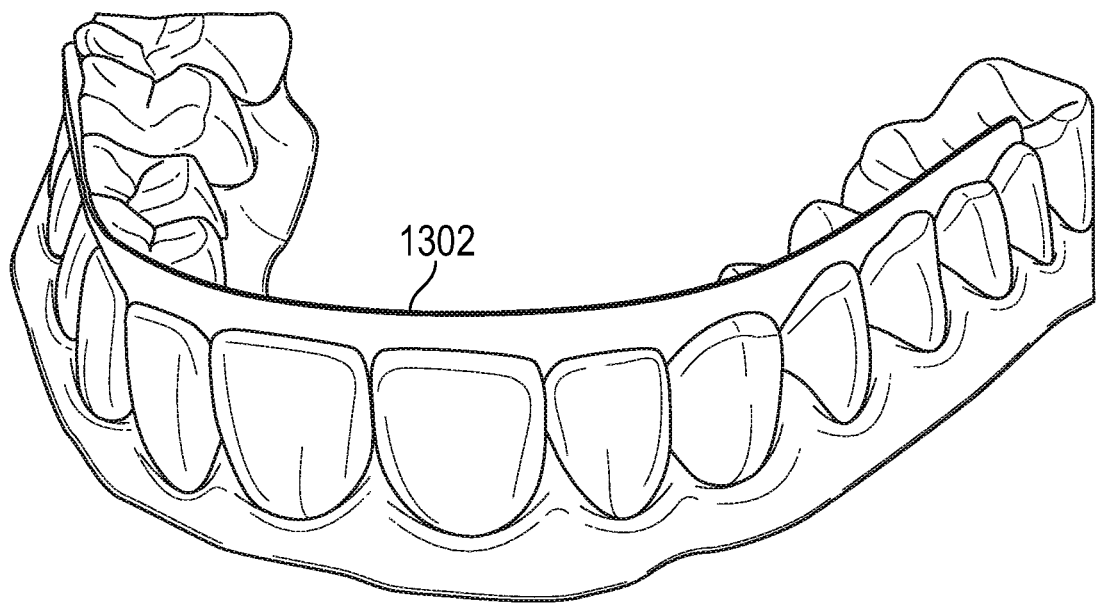
FIGS. 13A & 13B are conceptual diagrams illustrating example mold parting surfaces, in accordance with various aspects of this disclosure.
Figure 13B:
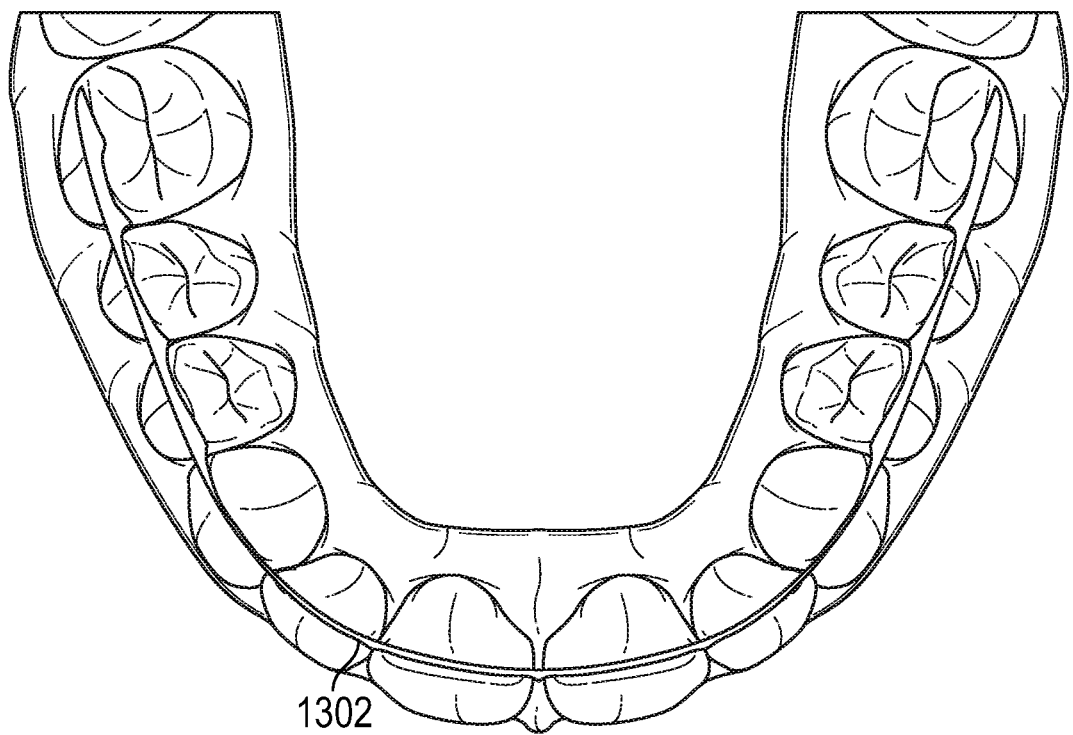

FIGS. 13A & 13B are conceptual diagrams illustrating example mold parting surfaces, in accordance with various aspects of this disclosure. Neural network engine 184 may generate mold parting surface 1302 based on landmarks such as a midpoint of each tooth and points between adjacent teeth (e.g., points of contact between adjacent teeth and/or points of closest approach between adjacent teeth) for each slice. In some examples, neural network engine may generate a 3D mesh of mold parting surface 1302 as part of the neural network-based placement generation techniques of this disclosure. Additional details of how mold parting surface 1302 can be used with respect to appliance manufacture are described in WO 2020/240351, filed May 20, 2020.

Figure 14:
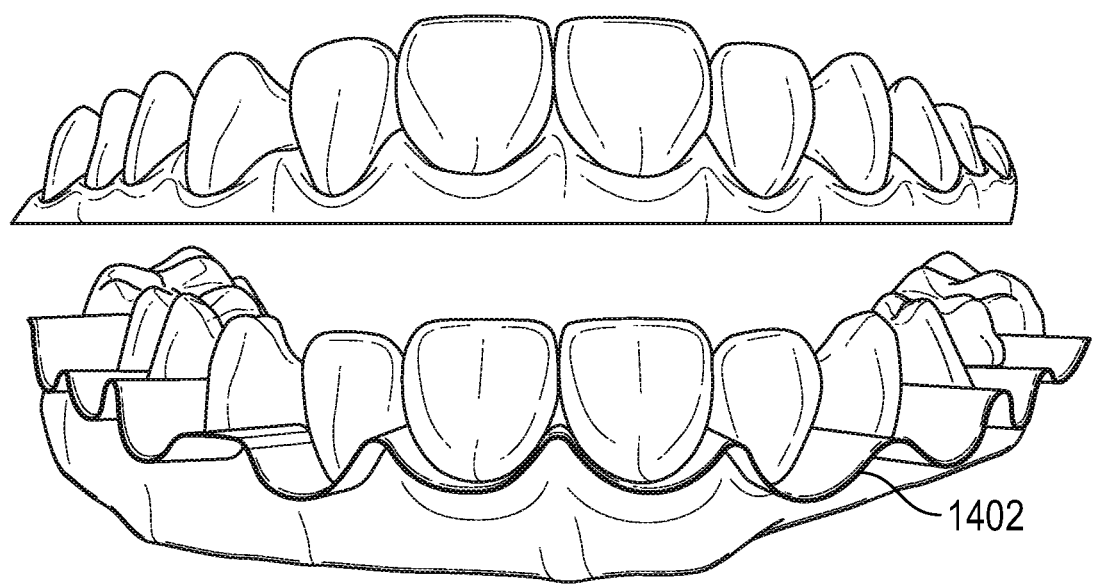
FIG. 14 is a conceptual diagram illustrating an example gingival trim surface, in accordance with various aspects of this disclosure.

FIG. 14 is a conceptual diagram illustrating an example gingival trim surface, in accordance with various aspects of this disclosure. Gingival trim surface 1402 may include a 3D mesh that trims an encompassing shell between the gingiva and the teeth in the illustrated dental anatomy.

Figure 15:
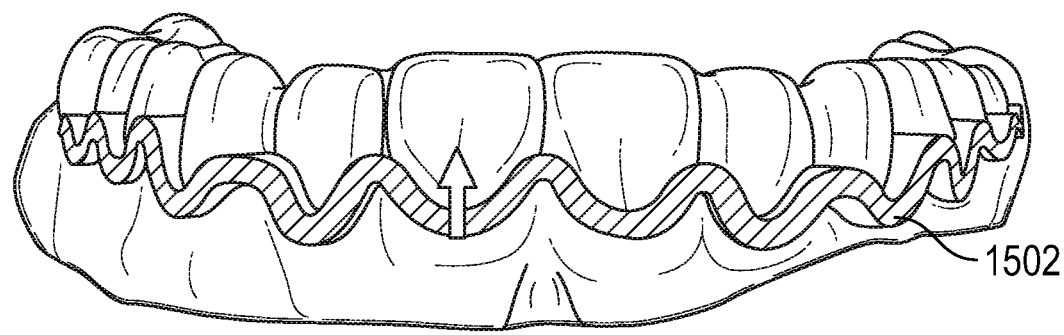
FIG. 15 is a conceptual diagram illustrating an example facial ribbon, in accordance with various aspects of this disclosure.

FIG. 15 is a conceptual diagram illustrating an example facial ribbon, in accordance with various aspects of this disclosure. Facial ribbon 1502 is a stiffening rib of nominal thickness that is offset facially from the shell. In some instances, the facial ribbon follows both the archform and the gingival margin. In one instance, the bottom of the facial ribbon falls no farther gingivally than the gingival trim surface.

Figure 16:
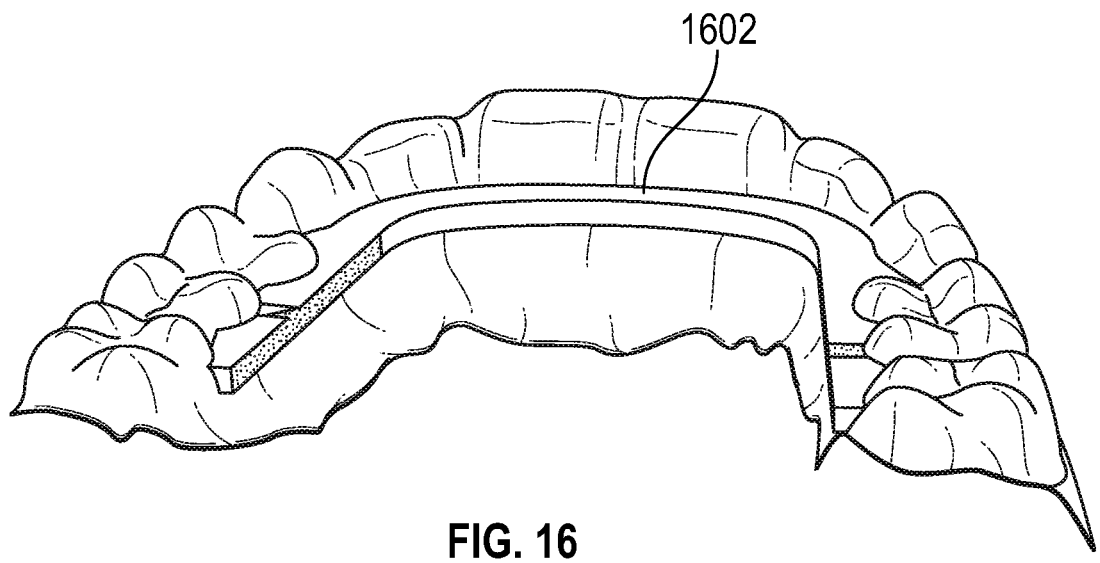
FIG. 16 is a conceptual diagram illustrating an example lingual shelf, in accordance with various aspects of this disclosure.

FIG. 16 is a conceptual diagram illustrating an example lingual shelf 1602, in accordance with various aspects of this disclosure. Lingual shelf 1602 is a stiffening rib of nominal thickness on the lingual side of the mold appliance, inset lingually and following the archform.

Figure 17:
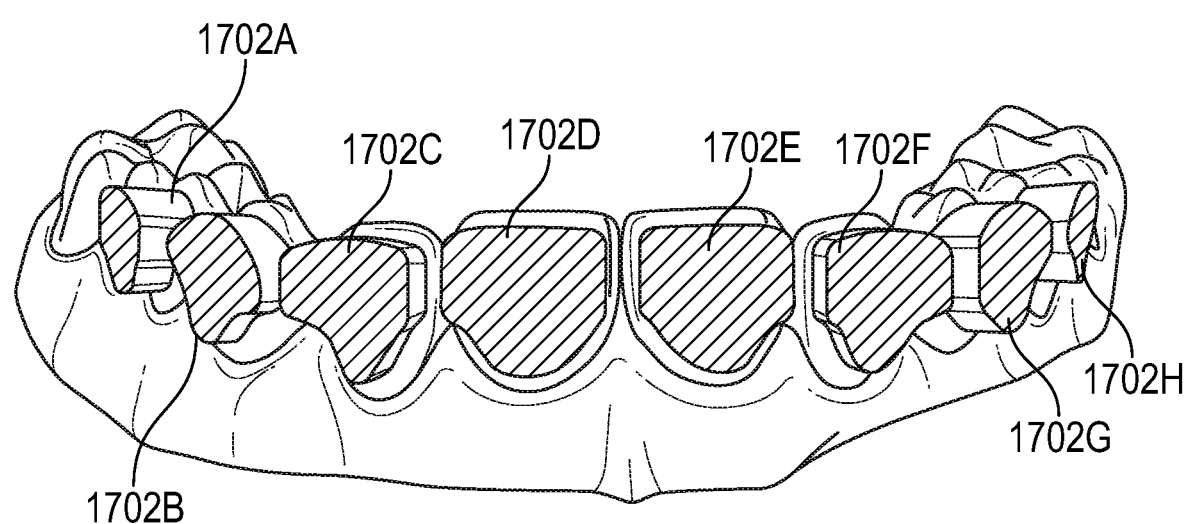
FIG. 17 is a conceptual diagram illustrating example doors and windows, in accordance with various aspects of this disclosure.

FIG. 17 is a conceptual diagram illustrating example doors and windows, in accordance with various aspects of this disclosure. Windows 1704A-1704H (collectively, windows 1704) includes an aperture that provides access to the tooth surface so that dental composite can be placed on the tooth. A door includes a structure that covers the window. The shape of the window may be defined as a nominal inset from the perimeter of the tooth when viewing the tooth facially. In some instances, the shape of the door corresponds to the shape of a window. The door may be inset to create clearance between the door and window.

Figure 18:
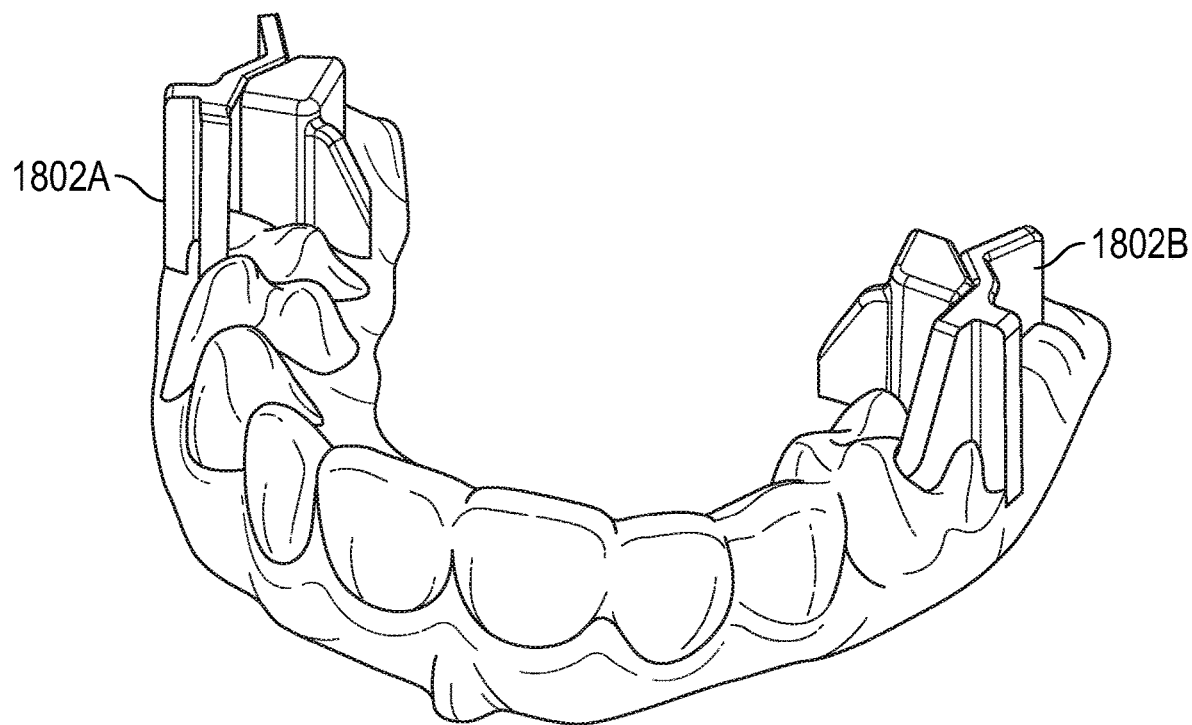
FIG. 18 is a conceptual diagram illustrating example rear snap clamps, in accordance with various aspects of this disclosure.

FIG. 18 is a conceptual diagram illustrating example rear snap clamps, in accordance with various aspects of this disclosure. Neural network 184 may determine one or more characteristics (e.g., placement-related or geometry-related characteristics) of rear snap clamps 1802A & 1802B (collectively, "rear snap clamps 1802"). Rear snap clamps 1802 may be configured to couple a facial portion of dental appliance 112 with a lingual portion of dental appliance 112. Example characteristics include one or more of a size, shape, position, or orientation of rear snap clamps 1802. Position information for rear snap clamps 1802 may be along the archform on opposite ends of the archform (e.g., a first snap clamp at one end and a second snap clamp at another end). In some examples, a female portion of rear snap clamps 1802 may be positioned on the lingual side of the parting surface and a male portion of rear snap clamps 1802 may be positioned on the facial side.

Figure 19:
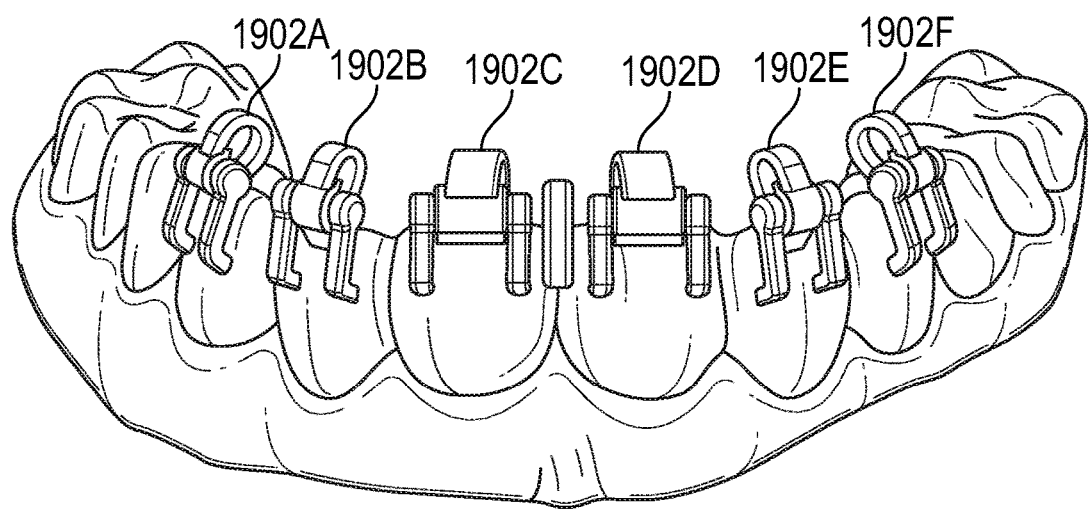
FIG. 19 is a conceptual diagram illustrating example door hinges, in accordance with various aspects of this disclosure.

FIG. 19 is a conceptual diagram illustrating example door hinges, in accordance with various aspects of this disclosure. Neural network engine 184 may determine one or more characteristics of door hinges 1902A-1902F (collectively, door hinges 1902) as part of generating placement and/or geometry information for dental appliance 112 in accordance with various aspects of this disclosure. Door hinges 1902 may be configured to pivotably couple a door to dental appliance 112. Example characteristics include one or more of size, shape, position, or orientation of the respective door hinge(s) 1902. The neural network executed by neural network engine 184 may position door hinges 1902 based on a position of another pre-defined appliance feature, in some non-limiting use case scenarios. For example, the neural network may position each door hinge 1902 at the midline of a corresponding door. In one use case scenario, the female portion of a respective door hinge 1902 may be positioned to anchor to the facial portion of dental appliance 112 (e.g., towards the incisal edge of a respective tooth) and the male portion of the same door hinge 1902 may be positioned to anchor to the outer face of the door.

Figure 20A:
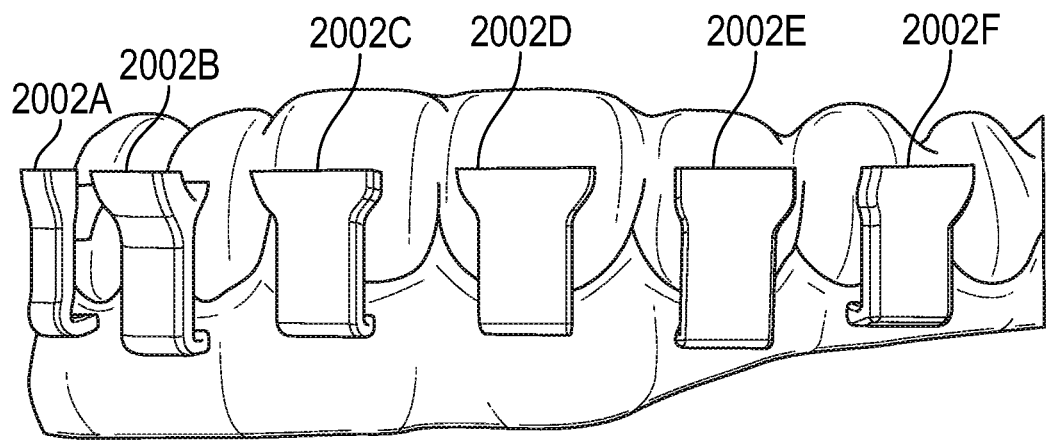
FIGS. 20A & 20B are conceptual diagrams illustrating example door snaps, in accordance with various aspects of this disclosure.
Figure 20B:
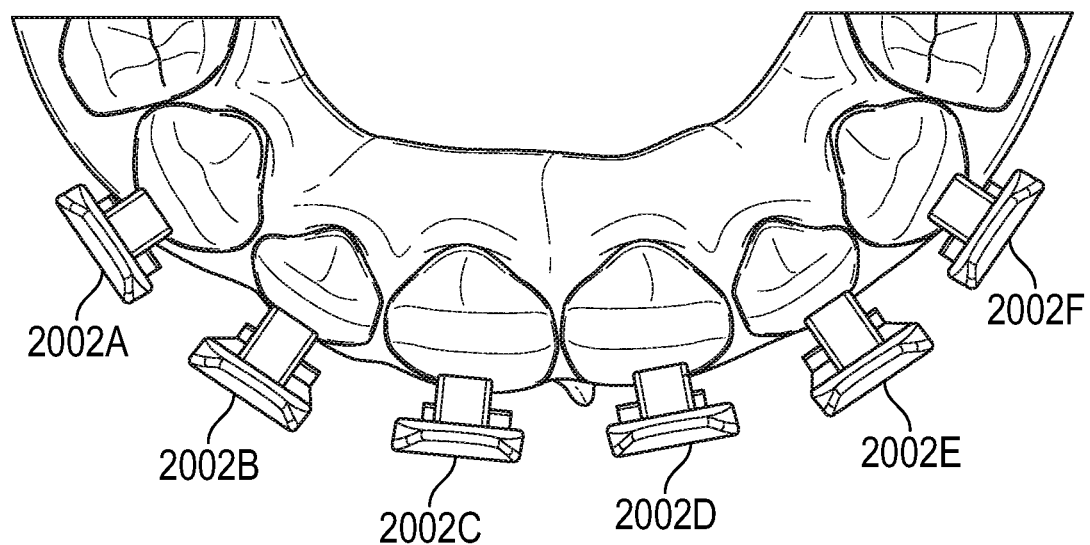

FIGS. 20A & 20B are conceptual diagrams illustrating example door snaps, in accordance with various aspects of this disclosure. Neural network engine 184 may determine one or more characteristics of door snaps 2002A-2002F (collectively, "door snaps 2002"), such as placement characteristics and/or geometry characteristics. Example characteristics include one or more of size, shape, position, or orientation of the door snaps 2002. In some examples, the neural network executed by neural network engine 184 may determine the position of door snaps 2002 based on a position of another pre-defined appliance feature. In one example, the neural network may generate a placement profile that positions each door snap 2002 at the midline of a corresponding door. In one example, the position of the female portion of a particular door snap 2002 may be anchored to an outer face of the door and extends downward toward the gingiva. In another example, the male portion of a particular door snap 2002 may be anchored to the gingival side of the facial ribbon.

Figure 21:
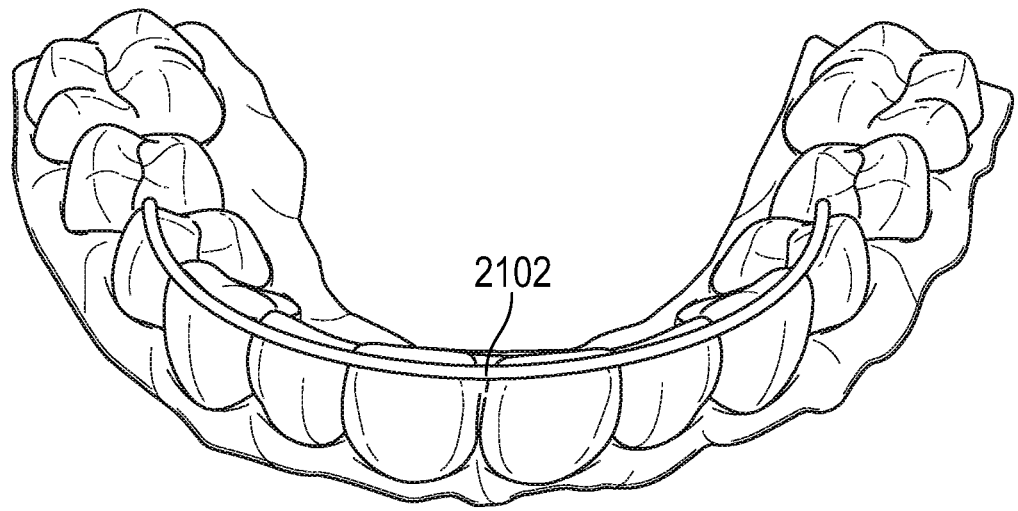
FIG. 21 is a conceptual diagram illustrating an example incisal ridge, in accordance with various aspects of this disclosure.

FIG. 21 is a conceptual diagram illustrating an example incisal ridge, in accordance with various aspects of this disclosure. Incisal ridge 2102 provides reinforcement at the incisal edge.

Figure 22:
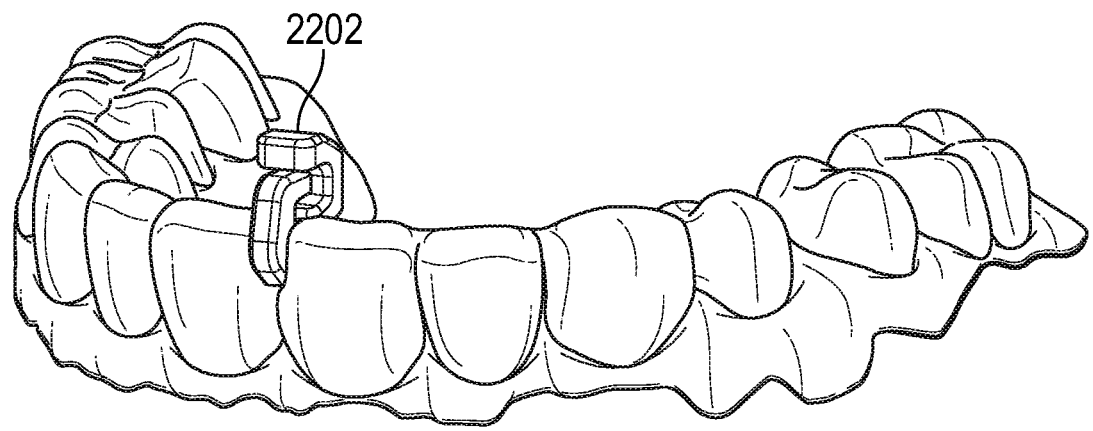
FIG. 22 is a conceptual diagram illustrating an example center clip, in accordance with various aspects of this disclosure.

FIG. 22 is a conceptual diagram illustrating an example center clip, in accordance with various aspects of this disclosure. Center clip 2202 aligns the facial portion and the lingual portion of the dental appliance with one another.

Figure 23:
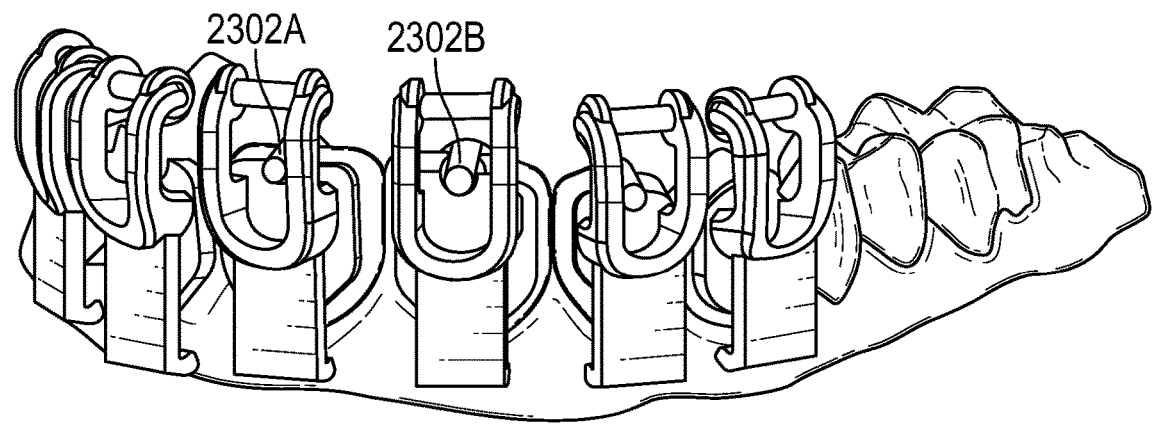
FIG. 23 is a conceptual diagram illustrating example door vents, in accordance with various aspects of this disclosure.

FIG. 23 is a conceptual diagram illustrating example door vents, in accordance with various aspects of this disclosure. Door vents 2302A-2302B (collectively, "door vents 2302") transport excess dental composite out of the dental appliance.

Figure 24:
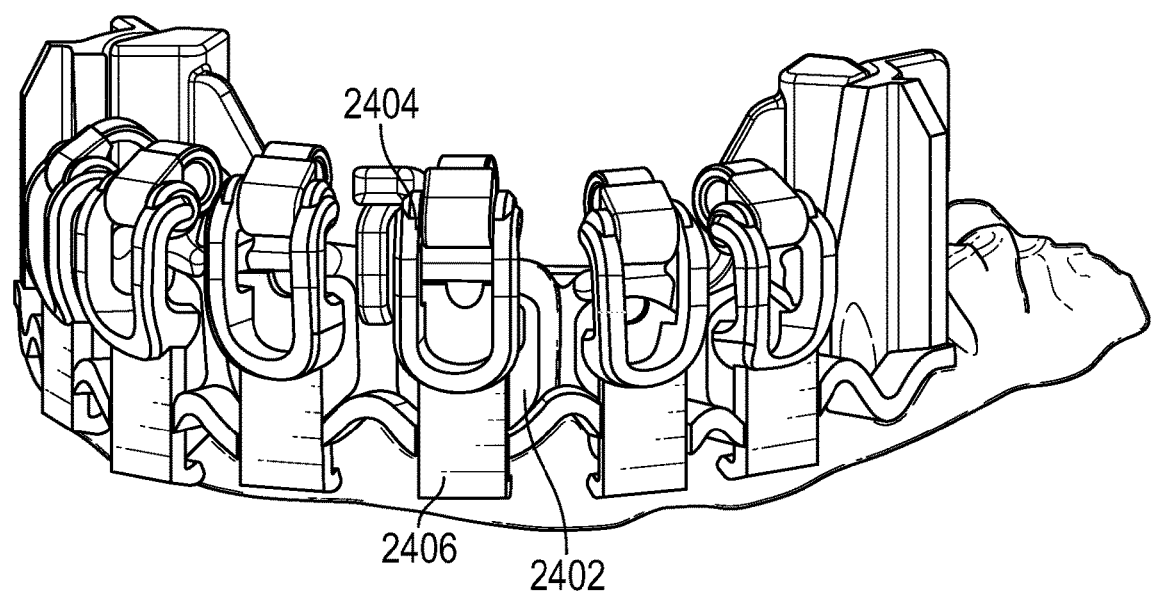
FIG. 24 is a conceptual diagram illustrating example doors, in accordance with various aspects of this disclosure.

FIG. 24 is a conceptual diagram illustrating example doors, in accordance with various aspects of this disclosure. In the example of FIG. 24, a dental appliance includes door 2402, door hinge 2404, and door snap 2406.

Figure 25:
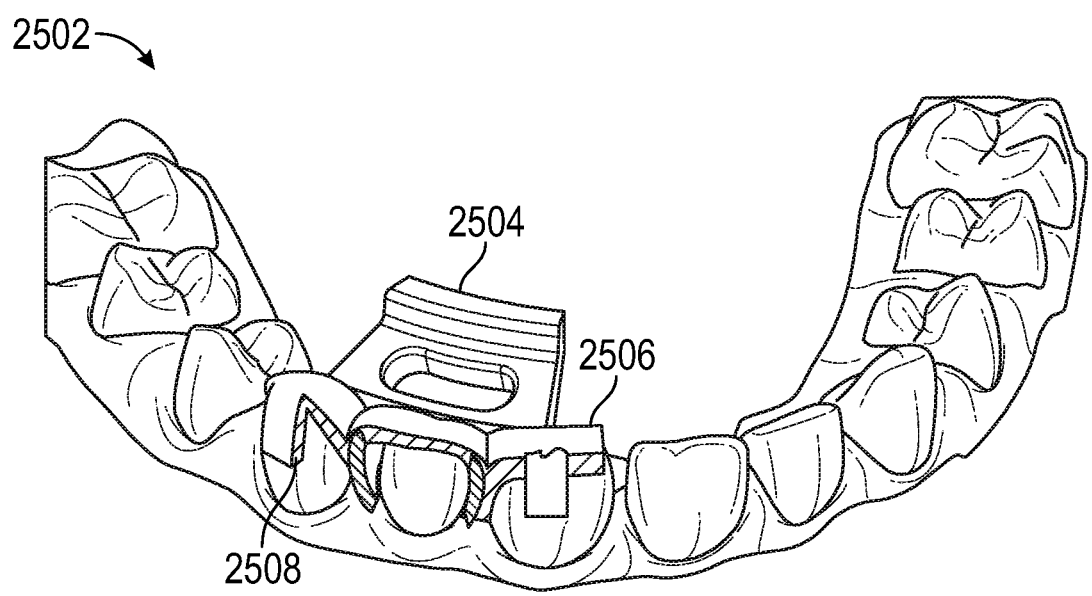
FIG. 25 is a conceptual diagram illustrating an example diastema matrix, in accordance with various aspects of this disclosure.

FIG. 25 is a conceptual diagram illustrating an example diastema matrix, in accordance with various aspects of this disclosure. Diastema matrix 2502 includes handle 2504, body 2506, and wrapping portion 2508. Wrapping portion 2508 is configured to fit in the interproximal region between two adjacent teeth.

Figure 26:
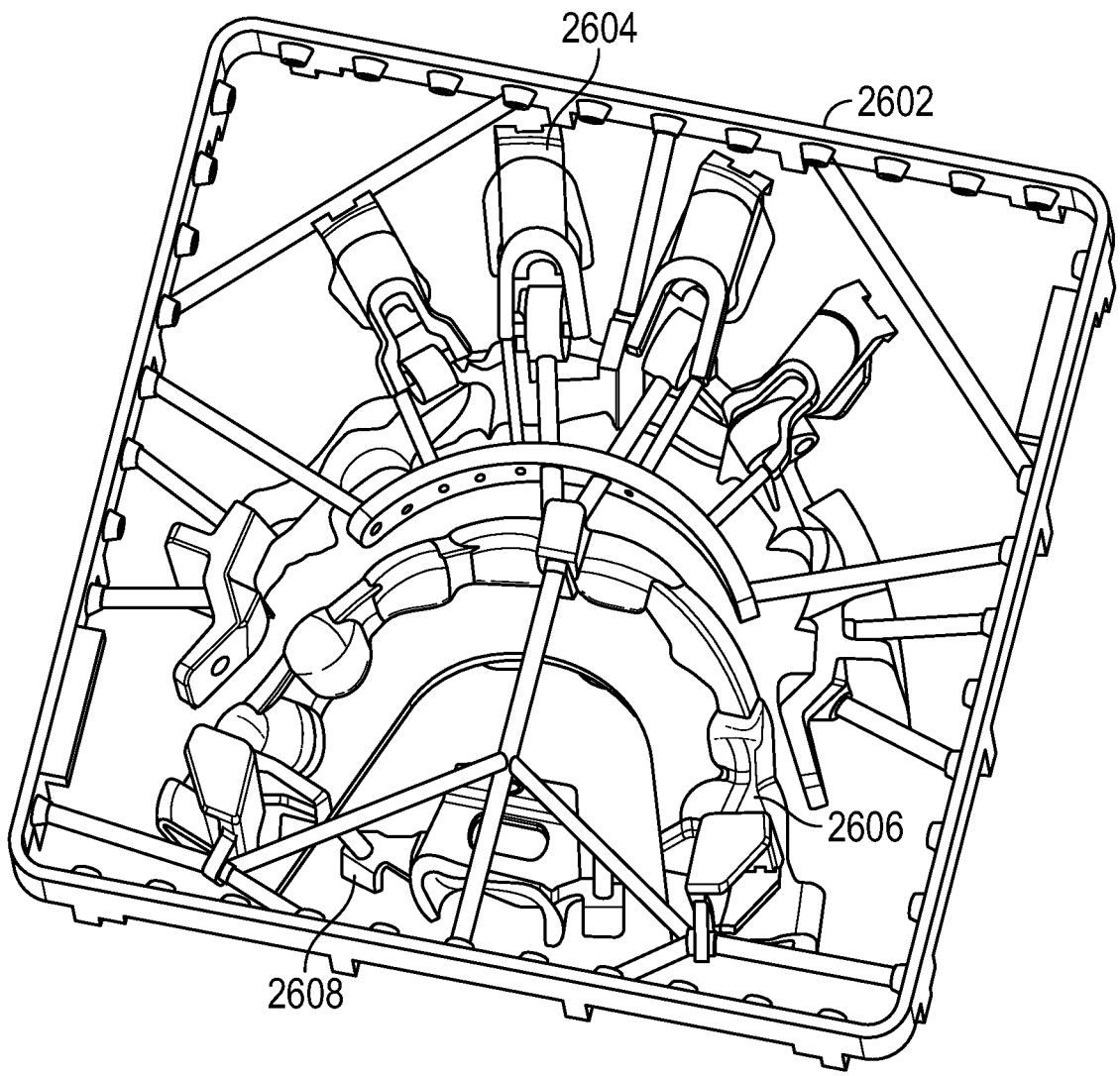
FIG. 26 is a conceptual diagram illustrating an example manufacturing case frame and an example dental appliance, in accordance with various aspects of this disclosure.

FIG. 26 is a conceptual diagram illustrating an example manufacturing case frame and an example dental appliance, in accordance with various aspects of this disclosure. Manufacturing case frame 2602 is configured to support one or more parts of a dental appliance. For example, the manufacturing case frame 2602 may detachably couple a lingual portion 2604 of a dental appliance, a facial portion 2606 of the dental appliance, and a diastema matrix 2608 to one another via case frame sparring 2610. In the example of FIG. 26, case frame sparring 2610 ties or couples the parts 2604, 2606, and 2608 of the dental appliance to the manufacturing case frame 2602.

Figure 27:
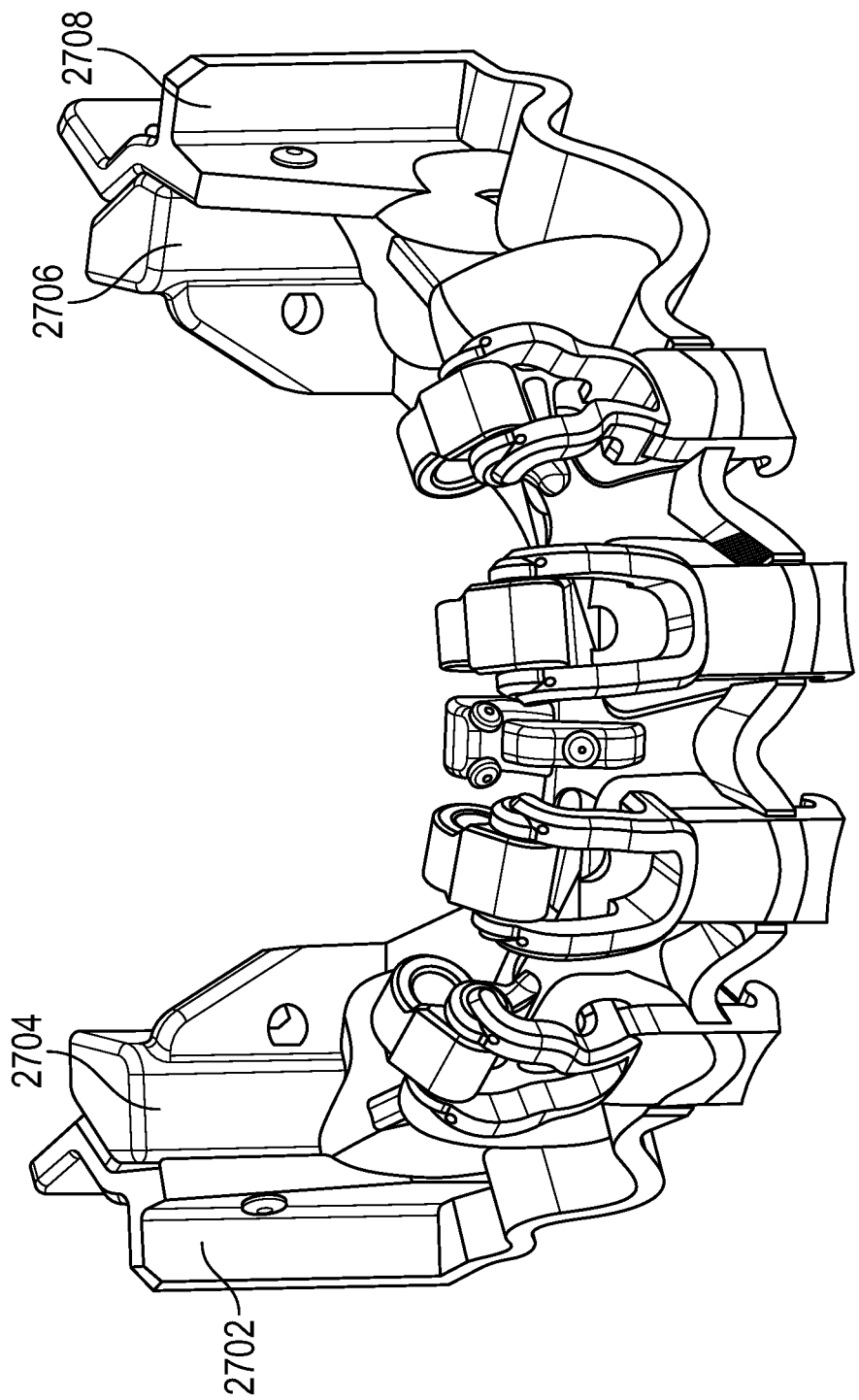
FIG. 27 is a conceptual diagram illustrating an example dental appliance including custom labels, in accordance with various aspects of this disclosure.

FIG. 27 is a conceptual diagram illustrating an example dental appliance including custom labels, in accordance with various aspects of this disclosure. Custom labels 2702-2708 may be printed on various parts of the dental appliance and includes data (e.g., a serial number, a part number, etc.) identifying a respective part of the dental appliance.

Various examples have been described. These and other examples are within the scope of the following claims.

What is claimed is:
1. A computing device comprising:
an input interface configured to receive one or more three-dimensional (3D) tooth meshes associated with a current dental anatomy of a dental restoration patient and a 3D component mesh representing a generated geometry for a dental appliance component; and
a neural network engine configured to:
provide the one or more 3D tooth meshes and the 3D component mesh received by the input interface as inputs to a neural network trained with training data comprising ground truth dental appliance component geometries and 3D tooth meshes of corresponding dental restoration cases; and
execute the neural network using the provided inputs to produce an updated model of the dental appliance component with respect to the current dental anatomy of the dental restoration patient.

2. The computing device of claim 1, wherein the neural network is a generative adversarial network (GAN) comprising a generator network and a discriminator network, and wherein to execute the neural network to produce the updated model of the dental appliance component with respect to the current dental anatomy of the dental restoration patient, the neural network engine is configured to provide the one or more 3D tooth meshes and the 3D component mesh received by the input interface as input to the generator network of the GAN.

3. The computing device of claim 2, wherein the neural network engine is configured to train the GAN by:
  executing the generator network of the GAN to generate an updated geometry of the dental appliance component using the one or more 3D tooth meshes and the 3D component mesh;
  providing the updated geometry of the dental appliance component, the one or more 3D tooth meshes, and the 3D component mesh as inputs to the discriminator network of the GAN; and
  executing the discriminator network to output a probability of the updated geometry representing a ground truth geometry.

4. The computing device of claim 1, wherein the neural network is further trained with placement information of the ground truth dental appliance component geometries as part of the training data.

5. The computing device of claim 1, wherein the dental appliance component comprises one or more of:
  a mold parting surface,
  a gingival trim,
  a door,
  a window,
  a facial ribbon,
  an incisal ridge,
  a lingual shelf,
  a diastema matrix,
  a case frame,
  a part label;
  a door hinge,
  a door snap,
  a door vent,
  a snap clamp, or
  a center clip.

6. A method comprising:
  receiving, at an input interface, one or more three-dimensional (3D) tooth meshes associated with a current dental anatomy of a dental restoration patient and a 3D component mesh representing a generated geometry for a dental appliance component;
  providing, by a neural network engine communicatively coupled to the input interface, the one or more 3D tooth meshes and the 3D component mesh received by the input interface as inputs to a neural network trained with training data comprising ground truth dental appliance component geometries and 3D tooth meshes of corresponding dental restoration cases; and
  executing, by the neural network engine, the neural network using the provided inputs to produce an updated model of the dental appliance component with respect to the current dental anatomy of the dental restoration patient.

7. The method of claim 6, wherein the neural network is a generative adversarial network (GAN) comprising a generator network and a discriminator network, and wherein executing the neural network to produce the updated model of the dental appliance component with respect to the current dental anatomy of the dental restoration patient comprises providing, by the neural network engine, the one or more 3D tooth meshes and the 3D component mesh received by the input interface as input to the generator network of the GAN.

8. The method of claim 7, further comprising training, by the neural network engine the GAN by:
  executing the generator network of the GAN to generate an updated geometry of the dental appliance component using the one or more 3D tooth meshes and the 3D component mesh;
  providing the updated geometry of the dental appliance component, the one or more 3D tooth meshes, and the 3D component mesh as inputs to the discriminator network of the GAN; and
  executing the discriminator network to output a probability of the updated geometry representing a ground truth geometry.

9. The method of claim 6, wherein the neural network is further trained with placement information of the ground truth dental appliance component geometries as part of the training data.

10. The method of claim 6, wherein the dental appliance component comprises one or more of:
  a mold parting surface,
  a gingival trim,
  a door,
  a window,
  a facial ribbon,
  an incisal ridge,
  a lingual shelf,
  a diastema matrix,
  a case frame,
  a part label;
  a door hinge,
  a door snap,
  a door vent,
  a snap clamp, or
  a center clip.

11. A non-transitory computer-readable storage medium encoded with instructions that, when executed, cause one or more processors of a computing system to:
  receive, via an input interface of the computing system, one or more three-dimensional (3D) tooth meshes associated with a current dental anatomy of a dental restoration patient and a 3D component mesh representing a generated geometry for a dental appliance component;
  provide the one or more 3D tooth meshes and the 3D component mesh received via the input interface as inputs to a neural network trained with training data comprising ground truth dental appliance component geometries and 3D tooth meshes of corresponding dental restoration cases; and
  execute the neural network using the provided inputs to produce an updated model of the dental appliance component with respect to the current dental anatomy of the dental restoration patient.

12. The non-transitory computer-readable storage medium of claim 11, wherein the neural network is a generative adversarial network (GAN) comprising a generator network and a discriminator network,
  and wherein the instructions that cause the one or more processors to execute the neural network to produc the updated model of the dental applicance component with respect to the current dental anatomy of the dental restoration patient comprises instructions that, when executed, cause the one or more processors to provide the one or more 3D tooth meshes and the 3D component mesh received via the input interface as input to the generator network of the GAN.

13. The non-transitory computer-readable storage medium of claim 12, further encoded with instructions that, when executed by the one or more processors, train the GAN by:
- executing the generator network of the GAN to generate an updated geometry of the dental appliance component using the one or more 3D tooth meshes and the 3D component mesh;
- providing the updated geometry of the dental appliance component, the one or more 3D tooth meshes, and the 3D component mesh as inputs to the discriminator network of the GAN; and
- executing the discrominator network to outpout a probability of the updated geometry representing a ground truth geometry.

14. The non-transitory computer-readable storage medium of claim 11, wherein the neural network is further trained with placement information of the ground truth dental appliance component geometries as part of the training data.

15. The non-transitory computer-readable storage medium of claim 11, wherein the dental appliance component comprises one or more of:
- a mold parting surface,
- a gingival trim,
- a door,
- a window,
- a facial ribbon,
- an incisal ridge,
- a lingual shelf,
- a diastema matrix,
- a case frame,
- a part label;
- a door hinge,
- a door snap,
- a door vent,
- a snap clamp, or
- a center clip.

* * * * *